United States Patent
Surti et al.

(10) Patent No.: US 8,698,087 B2
(45) Date of Patent: Apr. 15, 2014

(54) LIMITED ANGLE TOMOGRAPHY WITH TIME-OF-FLIGHT PET

(75) Inventors: Suleman Surti, Philadelphia, PA (US); Joel S. Karp, Glenside, PA (US)

(73) Assignee: The Trustees of the University of Pennsylvania, Philadelphia, PA (US)

(*) Notice: Subject to any disclaimer, the term of this patent is extended or adjusted under 35 U.S.C. 154(b) by 1196 days.

(21) Appl. No.: 12/611,738

(22) Filed: Nov. 3, 2009

(65) Prior Publication Data

US 2010/0108896 A1  May 6, 2010

Related U.S. Application Data

(60) Provisional application No. 61/110,868, filed on Nov. 3, 2008.

(51) Int. Cl.
*G01T 1/00* (2006.01)
*G01T 1/16* (2006.01)

(52) U.S. Cl.
USPC ............ 250/363.04; 250/363.05; 250/363.03; 378/4

(58) Field of Classification Search
USPC ............ 250/363.04, 363.03, 363.05, 363.08; 378/10, 7, 8, 11, 15, 4
See application file for complete search history.

(56) References Cited

U.S. PATENT DOCUMENTS

| 6,114,703 | A * | 9/2000 | Levin et al. ................... 250/367 |
| 6,577,890 | B1 * | 6/2003 | Hayes et al. .................. 600/436 |
| 7,864,917 | B2 * | 1/2011 | Ribbing et al. ................. 378/9 |
| 2008/0007173 | A1 * | 1/2008 | Yamaguchi et al. ........... 313/527 |
| 2008/0073541 | A1 * | 3/2008 | Vija et al. ................. 250/363.05 |
| 2008/0237475 | A1 * | 10/2008 | Michaud et al. ......... 250/363.03 |
| 2009/0324042 | A1 * | 12/2009 | Laurence et al. ............. 382/131 |

FOREIGN PATENT DOCUMENTS

WO  WO 2006/109203  10/2006
WO  WO 2008/084438  7/2008

OTHER PUBLICATIONS

Abbey et al., "Human-and model-observer performance in ramp-spectrum noise: Effects of regularization and object variability", J Opt Soc Am A, Mar. 2001, 18(3), 473-488.

Abbey et al., "Modeling visual detection tasks in correlated image noise with linear model observers", In Beutel J, Kundel HK, Metter RLV, eds. Handbook of Medical Imaging, vol. 1, Physics and Psychophysics, vol. 1., Bellingham, WA, SPIE Press, Feb. 16, 2000, 629-654.

Adam et al., "Investigation of scattered radiation in 3D whole-body positron emission tomography using Monte Carlo simulations", Phys Med Biol., Dec. 1999, 44(12), 2879-2895.

Adam et al., "Performance of a whole-body PET scanner using curve-plate NaI(TI) detectors", J Nucl Med., Dec. 2001, 42(12), 1821-1830.

(Continued)

*Primary Examiner* — David Porta
*Assistant Examiner* — Yara Green
(74) *Attorney, Agent, or Firm* — Baker & Hostetler LLP

(57) ABSTRACT

Provided are time-of-flight positron emission tomography devices comprising a detector array having at least two segments configured to accommodate a body part and to acquire tracer emission signals from a target within an imaging situs with a timing resolution of less than about 600 ps and a processor that receives the acquired signals from the detector array and converts the signals into a three dimensional image reconstruction of the target.

57 Claims, 15 Drawing Sheets

(56) References Cited

OTHER PUBLICATIONS

Alavi et al., "Implications of PET based molecular imaging on the current and future practice of medicine", Sem Nucl Med., Jan. 2004, 34(1), 56-69.
American Cancer Society, "Cancer Facts and Figures 2007", American Cancer Society, Inc., Atlanta, GA, © 2007, 1-56.
Avril et al., "Breast imaging with fluorine-18-FDG PET: Quantitative image analysis", J Nucl Med., Aug. 1997, 38(8), 1186-1191.
Avril et al., "Breast imaging with positron emission tomography and fluorine-18 fluorodeoxyglucose: Use and limitations", J Clin Oncol., Oct. 15, 2000, 18(20), 3495-3502.
Avril et al., "Metabolic characterization of breast tumors with positron emission tomography using F-18 fluorodeoxyglucose", J Clin Oncol., Jun. 1996, 14(6), 1848-1857.
Barrett et al., "Model observers for assessment of image quality", Proc Natl Acad Sci., Nov. 1, 1993, 90(21), 9758-9765.
Barrett et al., "Stabilized estimates of Hotelling-observer detection performance in patient-structured noise", SPIE Proceedings, Apr. 21, 1998, 3340, 27-43.
Berg et al., "High-Resolution Fluorodeoxyglucose Positron Emission Tomography with Compression ("Positron Emission Mammography") is Highly Accurate in Depicting Primary Breast Cancer", The Breast Journal, Jul.-Aug. 2006, 12(4), 309-323.
Budinger, "Time-of-Flight Positron Emission Tomography—Status Relative to Conventional PET", J Nucl Med., Jun. 1983, 24(1), 73-76.
Burgess et al., "Visual signal detectability with two noise components: Anomalous masking effects", J Opt Soc Am A., Sep. 1997, 14(9), 2420-2442.
Casey et al., "Multicrystal two dimensional BGO detector system for positron emission tomography", IEEE Trans Nucl Sci., Feb. 1, 1986, 33(1), 460-463.
Chen et al., "Front-end electronics for the CDF-II time-of-flight system", IEEE Trans Nucl Sci., Dec. 2003, 50(6), 2486-2490.
Conti et al., "First experimental results of time-of-flight reconstruction on an LSO PET scanner", Phys Med Biol., Oct. 7, 2005, 50(19), 4507-4526.
Doshi et al., "Design and evaluation of an LSO PET detector for breast cancer imaging", Med Phys., Jul. 2000, 27(7), 1535-1543.
Eckstein et al., "A practical guide to model observers for visual detection in synthetic and natural noisy image", In Beutel J, Kundel HK, Metter RLV, eds. Handbook of Medical Imaging, vol. 1, Physics and Psychophysics, vol. 1., Bellingham, WA, SPIE Press, Feb. 16, 2000, 593-628.
Freifelder et al., "Dedicated PET scanners for breast imaging", Phys Med Biol., Dec. 1997, 42(12), 2463-2480.
Freifelder et al., "First results of a dedicated breast PET imager (B-PET) using NaI(Tl) curve-plate detectors", Paper presented at 2001 IEEE Nuclear Science Symposium and Medical Imaging Conference, Nov. 2001, San Diego, CA (no more data available).
Gifford et al., "A comparison of human and model observers in multislice LROC studies", IEEE Trans Med Imag, Feb. 2005, 24(2), 160-169.
Gifford et al., "A comparison of human observer LROC and numerical observer ROC for tumor detection in SPECT images", IEEE Trans Nucl Sci., Aug. 1999, 46(4), 1032-1037.
Gifford et al., "Channelized Hotelling and human observer correlation for lesion detection in hepatic SPECT imaging", J Nucl Med., Mar. 2000, 41(3), 514-521.
Gifford et al., "Ga-67 tumor detection using penalized-EM with nonanatomical regularizers", Paper presented at Conference Record of 2002 Nuclear Science Symposium and Medical Imaging Conference, Nov. 10-16, 2002 (no more data available).
Hanson, "Detectability in computed tomographic image", Med Phys., Sep. and Oct. 1979, 6, 441-451.
Hoffman et al., "Quantitation in Positron Emission Computed-Tomography .1. Effect of Object Size", Journal of Computer Assisted Tomography, Jun. 1979, 3(3), 299-308.
Humm et al., "From PET detectors to PET scanners", Eur J Nucl Med., Nov. 2003, 30(11), 1574-1597.

Ishida et al., "Digital image processing: Effect on detectability of simulated low-contrast radiographic patterns", Radiology, Feb. 1984, 150(2), 569-575.
Karp et al., "Characterization of TOF PET scanner based on Lanthanum Bromide", Paper presented at: 2005 IEEE Nuclear Science Symposium and Medical Imaging Conference, Oct. 23-29, 2005, 5, San Juan, Puerto Rico, 1919-1923.
Karp et al., "Performance of a brain PET camera based on anger-logic gadolinium oxyrorthosilicate detectors", J Nucl Med., Aug. 2003, 44(8), 1340-1349.
Karp et al., "Performance of a Position-Sensitive Scintillation Detector", Phys Med Biol., Jul. 1985, 30(7), 643-655.
Khalkhali et al., "Diagnostic accuracy of Tc-99m-sestamibi breast imaging: Multicenter trial results", J Nucl Med., Dec. 2000, 41(12), 1973-1979.
Kolb et al., "Comparison of the performance of screening mammography, physical examination, and breast US and evaluation of factors that influence them: An analysis of 27,825 patient evaluations", Radiol., Oct. 2002, 225(1), 165-175.
Kuhn et al., "Design of a lanthanum bromide detector for time-of-flight PET", IEEE Trans Nucl Sci., Oct. 2004, 51(5), 2550-2557.
Kuhn et al., "Investigation of LaBr3 Detector Timing Resolution", Paper presented at 2005 IEEE Nuclear Science Symposium and Medical Imaging Conference, Oct. 23-29, 2005, San Juan, Puerto Rico, 5 pages.
Kyba et al., "Timing measurements from TOF-PET scanner using local PMT triggering", Paper presented at: 2007 IEEE Nuclear Science Symposium and Medical Imaging Conference, Oct. 26-Nov. 3, 2007, 6, 4123-4128, Honololu, Hawaii.
Lamare et al., "Design simulation of a rotating dual-headed PET/CT scanner for breast imaging", Paper presented at: IEEE Nuclear Science Symposium & Medical Imaging Conference, Oct. 23-29, 2005, Puerto Rico.
Levin et al., "Impact of high energy resolution detectors on the performance of a PET system dedicated to breast cancer imaging", Physica Medica. 2006, 21(Supplement 1), 28-34
MacDonald et al., "Contribution of time-of-flight information to limited angle positron tomography", IEEE Trans Nucl Sci., Feb. 1982, NS-29(1), 516-519.
Mankoff et al., "The High Count Rate Performance of a 2-Dimensionally Position-Sensitive Detector for Positron Emission Tomography", Phys Med Biol., Apr. 1989, 34(4), 437-456.
Matej et al., "Direct Fourier reconstruction with Fourier reprojection for fully 3-D PET", IEEE Trans Nucl Sci., Aug. 2001, 48(4), 1378-1385.
Matej et al., "Efficient 3D grids for image-reconstruction using spherically-symmetrical volume elements", IEEE Trans Nucl Sci., Aug. 1995, 42(4), 1361-1370.
Moriya et al., "Development of a position-sensitive detector for TOF-PET", Paper presented at 2007 IEEE Nuclear Science Symposium and Medical Imaging Conference, Oct. 26-Nov. 3, 20074, 2842-2846, Honolulu, HI.
Moses et al., "Fundamental limits of positron emission mammography", Nucl Instrum Meth A., Jan. 2003, 497(1), 82-89.
Moses et al., "PET camera designs for imaging breast cancer and axillary node involvement", J Nucl Med., May 1995, 36, 69P.
Moses et al., "Prospects for time-of-flight PET using LSO scintillator", IEEE Trans Nucl Sci., Jun. 1999, 46(3), 474-478.
Muehllehner et al., "Performance Parameters of a Positron Imaging Camera", IEEE Trans Nucl Sci., Feb. 1976, 23(1), 528-537.
Myers et al., "Addition of a channel mechanism to the ideal-observer model", J Opt Soc Am A., Dec. 12, 1987, 4, 2447-2457.
Myers et al., "Aperture optimization for emission imaging: Effects of spatially varying background", J Opt Soc Am A., Jul. 1990, 7(7), 1279-1293.
Myers, "Visual perception in correlated noise [PhD thesis], Tucson, AZ", University of Arizona, May 1985, 153 pages.
NEMA Standards Publication NU 2-2001, "Performance Measurements of Positron Emission Tomographs", Washington, DC, National Electrical Manufacturers Association, 2001, 47 pages.
Palmedo et al., "Scintimammography with technetium-99m methoxyisobutylisonitrile: results of a prospective European multicentre trial", Eur J Nucl Med., Apr. 1998, 25(4), 375-385.

(56) References Cited

OTHER PUBLICATIONS

Perkins et al., "Performance measurements of a pixelated NaI(Tl) PET scanner", IEEE Trans Nucl Sci., Jun. 2003, 50(3), 373-377.
Popescu, "Iterative image reconstruction using geometrically ordered subsets with list-mode data", Paper presented at 2004 IEEE Nuclear Science Symposium and Medical Imaging Conference, Oct. 16-22, 2004, Rome, Italy, vol. 6, 3536-3540.
Quon et al., "FDG-PET and beyond: Molecular breast cancer imaging", J Clin Oncol., Mar. 10, 2005, 23(8), 1664-1673.
Raylman et al., "Comparison of scintillators for positron emission mammography (PEM) systems", IEEE Trans Nucl Sci., Feb. 2003, 50(1), 42-49.
Raylman et al., "Pixelated NaI(Tl) arrays for use in Positron Emission Mammography (PEM)", J. Nucl. Med., May 2002 Supplement, 43(5), p. 11P.
Raylman et al., "Positron emission mammography-guided breast biopsy", J Nucl Med., Jun. 2001, 42(6), 960-966.
Raylman et al., "The potential role of positron emission mammography for detection of breast cancer. A phantom study", Med Phys., Aug. 2000, 27(8), 1943-1954.
Samson et al., "Should FDG PET be used to decide whether a patient with an abnormal mammogram or breast finding at physical examination should undergo biopsy?", Acad Radiol., Jul. 2002, 9(7), 773-783.
Srinivas et al., "A Dedicated Breast Positron Emission Tomography (B-PET) Scanner: Characterization and Pilot Patient Study", Presentation Poster, Nov. 2006, 1 page.
Surti et al., "A count-rate model for PET scanners using pixelated Anger-logic detectors with different scintillators", Phys Med Biol., Dec. 7, 2005, 50(23), 5697-5715.
Surti et al., "Design evaluation of A-PET: A high sensitivity animal PET camera", IEEE Trans Nucl Sci., Oct. 2003, 50(5), 1357-1363.
Surti et al., "Evaluation of pixelated NaI(Tl) detectors for PET", IEEE Trans Nucl Sci., Feb. 2003, 50(1), 24-31.
Surti et al., "Image quality assessment of LaBr3-based whole-body 3D PET scanners: a Monte Carlo evaluation", Phys Med Biol., Oct. 7, 2004, 49(19), 4593-4610.
Surti et al., "Imaging characteristics of a 3-dimensional GSO whole-body PET camera", Journal of Nuclear Medicine, Jun. 2004, 45(6), 1040-1049.
Surti et al., "Imaging performance of A-PET: a small animal PET camera", IEEE Trans Med Imag., Jul. 2005, 24(7), 844-852.
Surti et al., "Investigation of time-of-flight benefit for fully 3-D PET", IEEE Trans Med Imag., May 2006, 25(5), 529-538.
Surti et al., "Measurements for TOF image quality gain in 3D PET and its implications for clinical imaging", J Nucl Med., May 1, 2006, 47(Supplement-1), 196P, 2 pages.
Surti et al., "Optimizing the performance of a PET detector using discrete GSO crystals on a continuous lightguide", IEEE Trans Nucl Sci., Jun. 2000, 47(3), 1030-1036.
Surti et al., "Performance of Philips Gemini TF PET/CT scanner with special consideration for its time-of-flight imaging capabilities", J Nucl. Med., Mar. 2007, 48(3), 471-480.
Tai et al., "MicroPET II: design, development and initial performance of an improved microPET scanner for small-animal imaging", Phys Med Biol., Jun. 7, 2003, 48(11), 1519-1537.
Tapiovaara et al., "SNR and noise measurements for medical imaging: I. A practical approach based on statistical decision theory", Phys Med Biol., Jan. 1993, 38(1) 1-92.
Tarantola et al., "PET instrumentation and reconstruction algorithms in whole-body applications", J Nucl Med., May 2003, 44(5), 756-769.
Thompson et al., "Feasibility Study for Positron Emission Mammography", Med Phys., Apr. 1994, 21(4), 529-538.
Thompson et al., "Positron Emission Mammography (PEM)—a Promising Technique for Detecting Breast-Cancer", IEEE Trans Nucl. Sci., Aug. 1995, 42(4), 1012-1017.
Torizuka et al., "Untreated primary lung and breast cancers: Correlation between F-18 FDG kinetic rate constants and findings of in vitro studies", Radiology, Jun. 1998, 207(3), 767-774.
Townsend et al., "A. 3-Dimensional Image-Reconstruction for a Positron Camera with Limited Angular Acceptance", IEEE Trans Nucl. Sci., Feb. 1980, 27(1), 463-470.
Vandenberghe et al., "Fast reconstruction of 3D time-of-flight PET data by axial rebinning and transverse mashing", Phys Med Biol., Mar. 2006, 51(6), 1603-1621.
Vandenberghe et al., "System characteristics of simulated limited angle TOF PET", Nucl. Instr Meth (A), Feb. 2007, 571(1-2), 480-483.
Wagner et al., "An assortment of image quality indices for radiographic film-screen combinations—Can they be resolved?", SPIE Proceedings, 1972, 35, 83-94.
Wahl, "Current status of PET in breast cancer imaging, staging, and therapy", Semin Roentg., Jul. 2001, 36(3), 250-260.
Weinberg et al., "Applications of a PET device with 1.5 mm FWHM intrinsic spatial resolution to breast cancer imaging", Paper presented at IEEE International Symposium on Biomedical Imaging: Macro to Nano, Apr. 15-18, 2004, 2, 1396-1399, Arlington, VA.
Weinberg et al., "Preliminary results for positron emission mammography: Real-time functional breast imaging in a conventional mammography gantry", Eur. J. Nucl. Med., Jul. 1996, 23(7), 804-806.
Werner et al., "Implementation and Evaluation of a 3D PET Single Scatter Simulation with TOF Modeling", Paper presented at: 2006 IEEE Nuclear Science Symposium and Medical Imaging Conference, Oct. 29-Nov. 1, 2006, San Diego, CA, 1768-1773.
Wollenweber et al., "Comparison of Hotelling observer models and human observers in defect detection from myocardial SPECT imaging", IEEE Trans Nucl. Sci., Dec. 1999, 46(6), 2098-2108.
Wong et al., "A 2-Dimensional Detector Decoding Study on Bgo Arrays with Quadrant Sharing Photomultipliers", IEEE Trans Nucl. Sci., Aug. 1994, 41(4), 1453-1457.
Wong et al., "An analog decoding BGO block detector using circular photomultipliers", IEEE Trans Nucl. Sci., Aug. 1995, 42(8), 1095-1101.
Wong et al., "Characteristics of Small Barium Fluoride (BaF2) Scintillator for High Intrinsic Resolution Time-of-Flight Positron Emission Tomography", IEEE Trans Nucl. Sci., Feb. 1984, 31(1), 381-386.
Yang et al., "Depth of interaction resolution measurements for a high resolution PET detector using position sensitive avalanche photodiodes", Phys. Med. Biol., May 2006, 51(9), 2131-2142.
Yutani et al., "Comparison of FDG-PET with MIBI-SPECT in the detection of breast cancer and axillary lymph node metastasis", J. Comput. Assist. Tomogr., Mar.-Apr. 2000, 24(2), 274-280.

* cited by examiner

TOF

Non-TOF

Full Ring  Two-third Ring  Half Ring

A  B  C 1-mm spatial resolution  2-mm spatial resolution  3-mm spatial resolution Phantom on clinical scanner
A Phantom on BPET scanner
B Patient on BPET scanner
C (A)

1x1x10 mm³ crystals    2x2x10 mm³ crystals    3x3x10 mm³ crystals (B)

(A)

(B)

Full-ring scanner     2/3 ring scanner     1/2 ring scanner (A)

(B)

Full-ring scanner     2/3 ring scanner     1/2 ring scanner x axis = scan time (mins) ; y axis = SNR

US 8,698,087 B2

LIMITED ANGLE TOMOGRAPHY WITH TIME-OF-FLIGHT PET

CROSS REFERENCE TO RELATED APPLICATIONS

The present application claims priority to U.S. Provisional App. No. 61/110,868, filed Nov. 3, 2008, which is hereby incorporated by reference in its entirety.

GOVERNMENT RIGHTS

Research leading to the disclosed invention was funded in part by the U.S. National Institutes of Health, Grant No. R01-CA113941 (Joel S. Karp). Accordingly, the United States Government may have certain rights in the invention described herein.

TECHNICAL FIELD

The present invention pertains to, among other things, limited angle time-of-flight positron emission tomography.

BACKGROUND

Positron emission tomography (PET) is a powerful imaging modality that has had a major impact in oncology due to its ability in detecting disease, staging, assessing response to therapy, and identifying recurrent disease (1). In clinical whole-body PET imaging $^{18}$F-FDG is the most commonly used tracer for oncological studies where the primary task is the detection and quantification of lesions anywhere in the patient body. Although $^{18}$F-FDG is by far the most widely used tracer, new tracers are being developed for cancer diagnosis, detection of hypoxia, and angiogenesis. These applications promise to expand the role of PET even further in patient management and health care.

Breast cancer is the most prevalent form of cancer in women, with an incidence rate that is double that of the next higher form (lung cancer). The American Cancer Society (ACS) (2) estimates that that there will be 178,480 new cases of invasive breast cancer in women in USA in 2007. This represents 26% of all new cancer cases in women, with an expected mortality rate of 22%. In addition, the ACS also estimates the occurrence of another 62,030 new cases of the in situ type within the same year, about 85% of which will be of the ductal carcinoma in situ (DCIS) type. Several studies have shown that detection and treatment of breast cancer in the early stages leads to a decrease in breast cancer mortality rates (3-6). As a result, mammographic imaging with an average sensitivity rate of 80-90% is used as a screening tool for early detection of breast cancer. However, a recent study (7) of a large sample of patients has shown that the specificity of mammography is only 35.8% and results in a large fraction of false positive cases. PET imaging with its functional imaging capability can potentially play a complementary role in these situations.

Due to the general nature of routine clinical imaging, clinical whole-body PET scanners are designed to achieve reasonably good spatial resolution in the range of about 5-6-mm (8, 9) with large scanner ring diameters of about 90-cm. Breast imaging, on the other hand, is concerned with detecting, characterizing the nature, and monitoring the response of small tumors in the early pT1 (lesion size is as small as 5-mm or less (pT1a stage) (10) and pT2 (lesion size<2-cm) stages. In addition, due to the early stages of cancer onset, glucose and subsequent $^{18}$F-FDG uptake may also be low in these stages (10-13). Hence, a scanner with high spatial resolution is needed for accurately detecting the small lesions, while high scanner sensitivity provides accurate, quantitative images for short scan times. Poor spatial resolution and limited scanner sensitivity of clinical whole-body PET scanners, therefore, represent the most significant limitations in the use of PET as an important diagnostic application in breast imaging, since the ability to detect and quantify tumors<10-mm in size is greatly compromised (10, 14, 15). In fact, Avril, et. al. (10) have shown that the clinical detection sensitivity is <48% for all pT1 stage tumors and <13% for tumors <1-cm in size (pT1a and pT1b stages). The limited ability of clinical PET to detect and quantify the small, early stage, tumors therefore prevents its use for screening women for breast cancer (16).

As a result, whole-body PET is currently used primarily in the staging of breast cancer patients and determining the efficacy of treatment in these patients. However, the limited spatial resolution and sensitivity of these PET scanners prevents their use in characterizing and monitoring response of early stage tumors (stages I and II with lesion sizes<2 cm). Likewise, inadequate spatial resolution, limited scanner sensitivity, and the geometrical restrictions associated with whole-body scanners present early detection, efficacy, cost, and other practicality issues with respect to other localized sites of interest, for example, in the brain, prostate, or heart.

The cost of a small, high performance dedicated (e.g., breast, brain, prostate, cardiac) scanner would be significantly less than a clinical whole-body PET/CT due to the use of less detector material. In addition, the short scan times will also reduce the cost of an imaging study. A dedicated scanner has the advantage of reduced attenuation of coincident photons because they do not travel through intervening anatomical structures (such as the chest, in the case of breast imaging, which effects scanning sensitivity by factor of 10), and increased geometric efficiency due to a smaller ring diameter (about a factor of 4 for typical geometries).

SUMMARY

In one aspect, the present invention is directed to time-of-flight positron emission tomography devices comprising a detector array having at least two segments configured to accommodate a body part and to acquire tracer emission signals from a target within an imaging situs with a timing resolution of less than about 600 ps and a processor that receives the acquired signals from the detector array and converts the signals into a three-dimensional image reconstruction of the target. In exemplary embodiments, the detector array may occupy less than half, about half, or about ⅔ of a space defining a ring around the imaging situs. Also, the detector array may comprise separate detectors that are symmetrically distributed about a space defining a ring around the imaging situs. The detector array may also include separate detectors that are asymmetrically distributed about a space defining a ring around the imaging situs and that may be movable relative to one another. For example, the detector array may comprise two detectors, wherein the maximum distance between the detectors is no more than about 40 cm during the operation of the device. The detector array may be configured to accommodate breast imaging, cardiac imaging, brain imaging, or prostate imaging.

The detector array may include scintillator crystals of lutetium oxyorthosilicate, lutetium yttrium oxyorthosilicate, or lanthanum bromide, where each of the crystals has a length of about 10 to about 30 mm and an individual size of 4×6×20 mm³ or of 2×2×10 mm³. The crystals also may have a polished surface finish.

DETAILED DESCRIPTION OF ILLUSTRATIVE EMBODIMENTS

Figure 1:
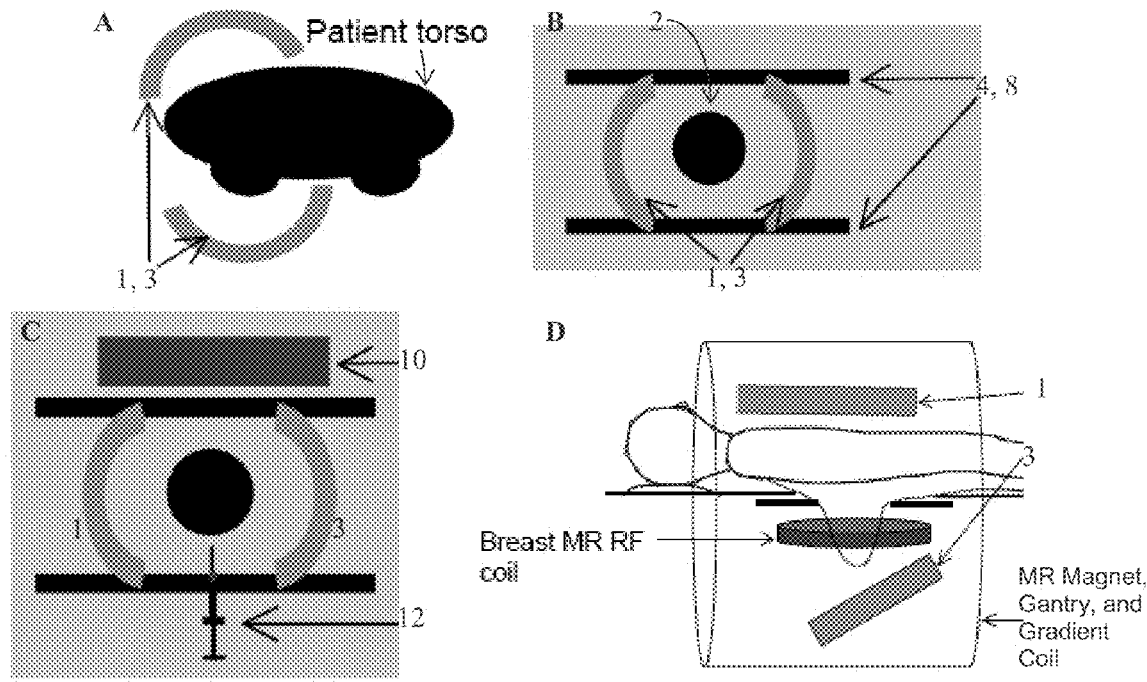
FIG. 1A provides a schematic showing a possible arrangement of detectors in front and back of female patient's chest for imaging small breasts and/or the axilla.
FIG. 1B is a top view schematic showing another arrangement including the underside of a horizontal gantry table with a circular cutout through which a patient's breast may hang in a location between the two detectors while the patient lies prone on top of the gantry table.
FIG. 1C provides a top view schematic showing the same arrangement as in FIG. 1B but also including a mammography detector.
FIG. 1D provides a side view of a device that incorporates an MRI coil and features a pair of PET detectors 1, 3 that are asymmetrically distributed about a space defining a ring around the breast imaging situs.

The present invention may be understood more readily by reference to the following detailed description taken in connection with the accompanying figures and examples, which form a part of this disclosure. It is to be understood that this invention is not limited to the specific products, methods, conditions or parameters described and/or shown herein, and that the terminology used herein is for the purpose of describing particular embodiments by way of example only and is not intended to be limiting of the claimed invention.

In the present disclosure the singular forms "a," "an," and "the" include the plural reference, and reference to a particular numerical value includes at least that particular value, unless the context clearly indicates otherwise. Thus, for example, a reference to "a detector" is a reference to one or more of such detectors and equivalents thereof known to those skilled in the art, and so forth. When values are expressed as approximations, by use of the antecedent "about," it will be understood that the particular value forms another embodiment. As used herein, "about X" (where X is a numerical value) preferably refers to ±10% of the recited value, inclusive. For example, the phrase "about 8" preferably refers to a value of 7.2 to 8.8, inclusive; as another example, the phrase "about 8%" preferably refers to a value of 7.2% to 8.8%, inclusive. Where present, all ranges are inclusive and combinable. For example, when a range of "1 to 5" is recited, the recited range should be construed as including ranges "1 to 4", "1 to 3", "1-2", "1-2 & 4-5", "1-3 & 5", "2-5", and the like. In addition, when a list of alternatives is positively provided, such listing can be interpreted to mean that any of the alternatives may be excluded, e.g., by a negative limitation in the claims. For example, when a range of "1 to 5" is recited, the recited range may be construed as including situations whereby any of 1, 2, 3, 4, or 5 are negatively excluded; thus, a recitation of "1 to 5" may be construed as "1 and 3-5, but not 2", or simply "wherein 2 is not included."

The disclosures of each patent, patent application, and publication cited or described in this document are hereby incorporated herein by reference, in their entirety.

Unless otherwise specified, italicized boldface numbers in parentheses (e.g., "(1)") correspond to the numbered list of references provided in the final paragraph of the present disclosure.

Detectors currently used in commercial PET scanners are discrete scintillator based detector designs with some form of light sharing technique like the pixelated Anger-logic detector (17) or the more popular blocksharing detector (18, 19). These detectors are typically used for decoding discrete 4-6 mm cross-section crystals (8, 9, 20), but have been modified with the use of an appropriate lightguide design and smaller photodetectors to discriminate crystals smaller than the 4×4 mm$^2$ cross-section as well (21, 22). There are other variants of detectors using small, discrete crystals that can also achieve the very good spatial resolution required for application-specific as well as small animal imaging PET scanners.

In recent years, dedicated partial ring PET devices (PEM, positron emission mammography) have been developed for use in breast imaging. These dedicated breast scanners use a variety of detector configurations and scintillators arranged in close proximity to the patient, which leads to a higher sensitivity than clinical PET scanners and reduced attenuation of photons traveling through the patient chest wall (23-31). The resolution of most of these scanners is in the range of 2-4 mm, with an emphasis on spatial resolution at the expense of sensitivity (short crystals) (23, 24, 27, 28). Commercially, a dedicated PEM device, the Flex Solo II from Naviscan PET Systems, has recently received FDA approval as well. This scanner uses 10 mm long lutetium-based crystals to achieve spatial resolution of <2 mm (32, 33). More recently proposed scanner designs utilize detectors capable of about 1-2-mm spatial resolution, high sensitivity (longer LSO scintillators), and depth-of-interaction (DOI) measurement capability (34, 35).

However, without detector rotation none of these devices produce an artifact-free tomographic image, thus the detection and quantification of small tumors is compromised. The reason for this is that the limited angle coverage of the imaging plane, due to a partial detector ring, leads to an incomplete sampling of the polar angles and produces artifacts in image reconstruction (36, 37). As a result, focal plane tomographic techniques (38) are used to produce 2D images in several parallel planes. As pointed out by others (39), the resultant images in these situations have a broad background, leading to reduced lesion contrast compared to a full tomographic reconstruction.

A partial ring design also reduces the sensitivity due to a loss of coincident events (⅔ of events are collected with a 120° coverage instead of a 180° coverage) and the use of potentially shorter crystals (coincidence stopping power of 10-15 mm long LSO crystals is ⅜-¾ that of 20 mm long LSO crystals that are typically used in clinical scanners). This translates into a total sensitivity gain of about a factor of 10-20 over a clinical scanner. Considering a typical scan time of 3-mins per single bed position (for imaging two breasts) on a clinical scanner, a dedicated breast scanner will, therefore, lead to much higher quality images in similar scan times. It is also notable that scans on a clinical PET scanner are normally performed for a whole-body imaging protocol, and so the total scan time on a clinical scanner is much longer (anywhere between 15-45 minutes). Besides the significant gain in sensitivity over a clinical PET scanner, a dedicated breast scanner will also have a much higher spatial resolution (1-2 mm as opposed to 5-6 mm in a clinical scanner) that allows the detection and quantification of small lesions (5 mm or less in diameter), a task which is practically impossible in reasonable scan times on a clinical scanner.

As disclosed herein, a dedicated PET scanner for use with respect to a localized body region (e.g., breast, prostate, brain, heart, lung, and the like) that produces tomographic images with very high spatial resolution and sensitivity relative to all-purpose whole-body PET scanners can play a significant role in the screening and staging cancer and other detectable conditions. For example, a dedicated breast scanner can provide quantitative tumor response measures due to the accurate uptake measurements (high spatial resolution) achieved in a dynamic imaging mode (high sensitivity). A dedicated PET scanner in accordance with the present invention can also serve as a component in a multi-modality imaging device; for example, a dedicated breast scanner may be used in combination with a mammography unit, optical scanner, or even magnetic resonance imaging (MRI).

Furthermore, dedicated scanner systems of the present invention may benefit from the aid of new tracers. Biologically, it is known that $^{18}$F-FDG may not be the ideal tracer for breast cancer imaging, but new tracers (14) developed to study processes such as cellular proliferation ($^{18}$F-FLT) and apoptosis ($^{18}$F labeled annexin V) in breast cancer, as well as estrogen receptor imaging for breast cancer ($^{18}$F-FES), may all benefit with the use of dedicated breast PET scanners, and such results may be obtained with respect to other types of dedicated scanner systems as disclosed herein.

The present invention may also benefit from experience that has been gained in connection with precursor systems. Previous systems have included a continuous NaI(Tl) based breast scanner (BPET) which performed an iterative limited angle reconstruction with reasonable success (40-42). This scanner was used to perform a pilot study of twenty patients and provided experience with respect to the challenges of dedicated breast imaging. The performance of the BPET scanner is, however, limited due to its spatial resolution (3-4 mm), moderate sensitivity, and limited count-rate capability. Also, the detector design limits access to the breast near the chest wall due to a 2 cm dead area near the detector edge. In dedicated breast imaging, just as in clinical whole-body imaging, an added effect on the ability to detect the small tumors is the amount of scatter and random coincidences from outside the field of view (FOV) which will add noise to the image (after an accurate bias subtraction). Most of these coincidences arise due to the high activity uptake in the heart and bladder. A recent Monte Carlo evaluation showed that even with appropriate shielding, the scatter fraction in a dedicated breast PET scanner is as high as 30% or more (43). Thus, for dedicated imaging in accordance with the present invention, including breast imaging, the primary instrumentation goals were high spatial resolution (1-2-mm) throughout the FOV, high sensitivity to allow fast and accurate imaging, tomographic reconstruction without detector rotation, and good energy resolution (for scatter and random coincidence rejection) for the detection and accurate quantification of small early stage lesions with low activity uptake.

In one aspect of the present invention, there are provided time-of-flight positron emission tomography devices comprising a detector array having at least two segments configured to accommodate a body part and to acquire tracer emission signals from a target within an imaging situs with a timing resolution of less than about 600 ps; and, a processor that receives the acquired signals from the detector array and converts the signals into a three dimensional image reconstruction of the target.

As shown herein, it has presently been discovered that a PET detector having a detector array that can acquire tracer emission signals with a timing resolution of less than about 600 ps can be used to provide high-quality images of an object within the imaging situs. Previous studies suggested that there was an absolute requirement for a timing resolution of less than 200 ps when the detector array occupies 74.4% of a space defining a ring around the imaging situs. See Crespo P, et al., *Direct time-of-flight for quantitative, real-time in-beam PET: a concept and feasibility study. Phys Med. Biol.* 2007 Dec. 7; 52(23):6795-811. The present devices may comprise a detector array that can acquire tracer emission signals with a timing resolution of less than about 600 ps, a timing resolution of about 300 ps to about 600 ps, or a timing resolution of less than about 300 ps. In some embodiments, the timing resolution is about 300 ps to about 600 ps, and the detector array occupies about 50% of a space defining a ring around the imaging situs. In other instances, the timing resolution is about 300 ps to about 600 ps, and the detector array occupies about ⅔ of a space defining a ring around the imaging situs. The timing resolution may be less than about 300 ps, and the detector array may occupy less than 50% of a space defining a ring around the imaging situs.

The present devices comprise a detector array having at least two segments. As used herein, a "segment" of the detector array is a PET detector that can act independently from other segments in the detector array, that can act cooperatively with one or more other segments in the detector array, or both. In one embodiment, the detector array comprises two segments. In other embodiments, the detector array may comprise three, four, five, or more than five segments. The segments may be identically sized and shaped, or may be differently sized, differently shaped, or both. The respective segments may be rectilinear (i.e., substantially "flat"), or curvilinear (i.e., convex or concave); a given detector array may comprise all rectilinear segments, all curvilinear segments, or a mixture of one or more rectilinear segments and one or more curvilinear segments.

The detector array may comprise at least two detectors and may be configured such that at least one detector segment is movable relative to at least one other detector segment. In such embodiments, the distance between two detector segments may be adjusted in order to accommodate a body part, to optimize imaging conditions, or both. In instances where the detector array comprises two detectors, during operation, the maximum distance between two detector segments may about 50 cm or less, about 45 cm or less, about 40 cm or less, about 35 cm or less, about 30 cm or less, about 25 cm or less (i.e., no more than about 25 cm), about 20 cm or less, about 15 cm or less, or about 10 cm or less. The detector array may also or alternatively be configured to accommodate the inclusion of one or more other components for obtaining information regarding the body part within the imaging situs. For example, the device may further comprise a mammography unit, an optical imaging array, or both. Such arrangements permit multi-modality analysis of a body part that can increase the clinical accuracy of the present devices to a degree that has not previously been possible. The detector array may also or alternatively be configured to permit access to the body part within the imaging situs by a tissue-sampling device, such as a biopsy syringe. In such embodiments, the information that is obtained using one or more of PET imaging, mammography, and optical imaging can be used to localize a site of interest within the body part, and a tissue sample may be obtained from the site of interest without removing the body part from the imaging situs within the detector array.

FIG. 1A provides a schematic showing a possible arrangement of detectors 1, 3 in front and back of female patient's chest for imaging small breasts and/or the axilla. FIG. 1B is a top view schematic showing another arrangement including the underside of a horizontal gantry table with a circular cutout 2 through which a patient's breast may hang in a location between the two detectors while the patient lies prone on top of the gantry table. Rails 4, 8 allow the distance between the two detectors to be adjusted. FIG. 1C provides a top view schematic showing the same arrangement as in FIG. 1B but also including a mammography detector 10 that is placed perpendicular to the PET detectors 1, 3 and that can be used to help guide the biopsy syringe 12 from the opposing space between detectors 1, 3. Thus, FIG. 1C shows schematically how a mammography unit or optical imaging unit can be integrated with the present devices for imaging, performing biopsy, or both. The device of FIG. 1C can also be used for cross-registering PET images with the planar X-ray image for dual modality imaging. FIG. 1D provides a side view of a device that incorporates an MRI coil and features a pair of PET detectors 1, 3 that are asymmetrically distributed about a space defining a ring around the breast imaging situs. The use of TOF information to produce artifact-free tomographic images for a dedicated, non-rotating, PET (and optionally multi-modal) scanner is newly disclosed herein. Imaging using the present devices may be performed while maintaining a very high spatial resolution (e.g., 1-2 mm) and high sensitivity (e.g., scan times of 5 minutes or less for detection and quantification of <5 mm diameter lesions).

The detector array, and collectively the segments of the detector array, may occupy at least a portion of a space defining a ring around an imaging situs. The "ring" around the imaging situs does not represent a physical element, but is rather a conceptual tool that is of assistance in describing the manner in which the detector array (and the segments thereof) is distributed about the imaging situs. The ring around the imaging situs may be described as an imaginary shape (regular or irregular), the outlines of which define the manner in which the detector array is distributed around the imaging situs. The "ring" may be substantially circular, elliptical, an irregular or regular polygon, a regular polygon with equal sides, or an irregular shape, and the detector array may substantially conform to at least a portion of the imaginary outlines thereof. For example, if the ring defines an ellipse, then the segments of the detector array may be roughly distributed around the imaginary outline of the ellipse. The distribution of the segments of the detector array about a space defining a ring around the imaging situs may be symmetrical or asymmetrical. For example, if the ring defines an ellipse and the detector array consists of two segments, then the two segments may respectively be located on directly opposite sides of the ellipse (for example, on opposite sides of the major axis, or on opposite sides of the minor axis of the ellipse), or the two segments may be offset relative to one another along the imaginary outline of the ellipse.

Figure 2:
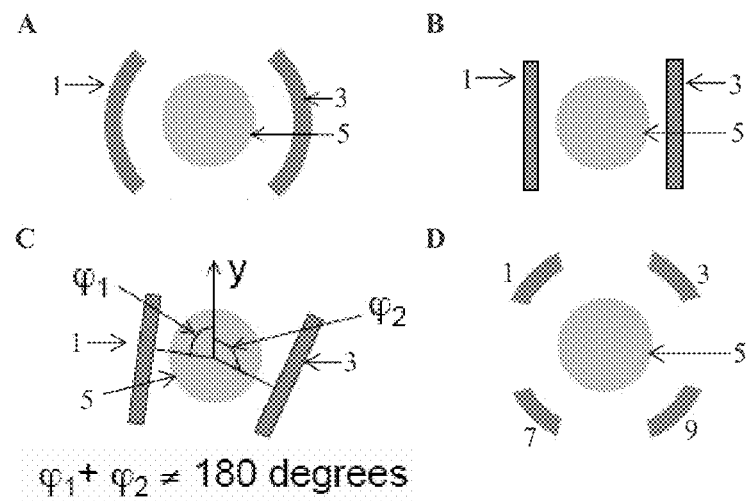
FIG. 2 provides several nonlimiting examples of the arrangement of the segments of the detector array around an imaging situs.

FIG. 2 provides several nonlimiting examples of the arrangement of the segments of the detector array around an imaging situs. FIG. 2A depicts an overhead view of an arrangement whereby a pair of curvilinear detector array segments 1, 3 are symmetrically distributed about a space defining a substantially circular ring around an imaging situs 5. FIG. 2B depicts an overhead view of an arrangement whereby a pair of rectilinear detector array segments 1, 3 are symmetrically distributed about a space defining a substantially regular polygon with four equal sides around an imaging situs 5. In FIGS. 2A and 2B, the detector array occupies about 50% of the space defining the ring around the imaging situs. FIG. 2C depicts an overhead view of an arrangement whereby a pair of rectilinear detector array segments 1, 3 are asymmetrically distributed about a space defining an irregular polygon around an imaging situs 5. FIG. 2D depicts an overhead view of an arrangement whereby four curvilinear detector array segments 1, 3, 7, 9 are symmetrically distributed about a space defining a substantially circular ring around an imaging situs 5.

The detector array of the present devices is configured to accommodate a body part. The "segmented" arrangement of the detector array is conducive to the accommodation of discrete body part (as used herein, a "body part" can refer to any extremity, limb, organ, group of organs, body region, or portion of a human body that is less than the whole), allowing specialized use of the present devices in a manner that a whole-body scanning apparatus cannot provide. For example, the detector array may be configured to accommodate a breast, for cardiac imaging, for brain imaging, or for prostate imaging.

Figure 3:
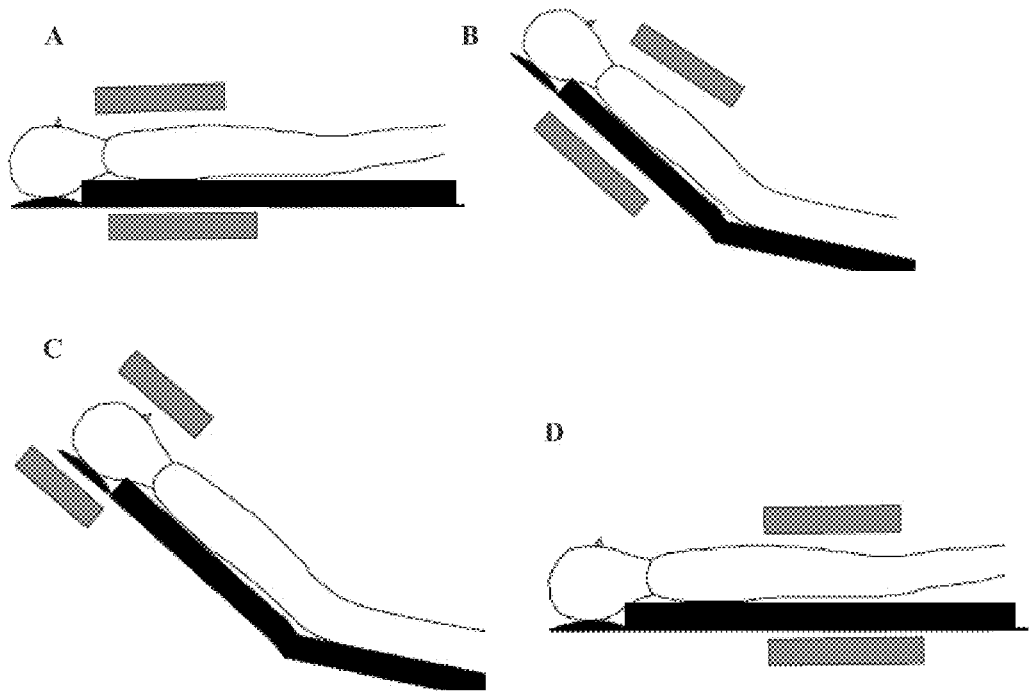
FIG. 3 depicts exemplary device configurations for cardiac imaging (FIG. 3A, 3B), brain imaging (FIG. 3C), and prostate imaging (FIG. 3D).

High spatial resolution detectors with DOI measurement are currently being developed by other research groups for use in dedicated breast scanners (34, 35). However, due to the limited angle geometry, these breast scanners are restricted in their ability to produce artifact-free tomographic images (without detector rotation) which are important for clinical diagnosis. For the instant scanner design (whether configured for breast imaging or for imaging of another body part), a partial ring scanner geometry is adopted for three reasons: it allows the flexibility to image the whole body part (in the case of a breast, including chest wall and possibly the axilla), it provides the ability to perform needle biopsy while a patient is in the scanner, and the ability to combine the PET scanner into a future multi-modality instrument with an optical imaging, mammography machine, and/or MRI device. See, e.g., FIGS. 1A-1D. FIG. 3 depicts exemplary configurations for cardiac imaging (FIG. 3A, 3B), brain imaging (FIG. 3C), and prostate imaging (FIG. 3D).

Figure 4:
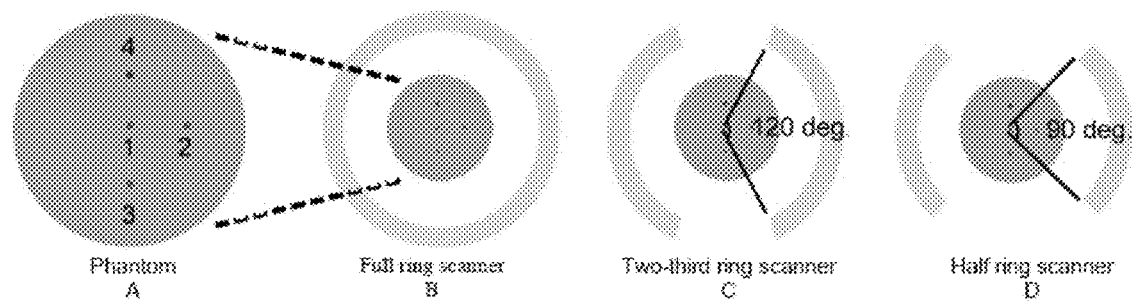
FIG. 4 illustrates the set-up of three simulated scanner designs: (B) a full ring; (C) a ⅔ ring (120° in-plane angular coverage); and, (D) a ½ ring (90° in-plane angular coverage; the simulated phantom (A) is 10 cm diameter×8 cm long cylinder, and contains three 5 mm hot lesions (labeled 1, 2, 3), and a cold 5 mm diameter lesion (labeled 4).
Figure 5:
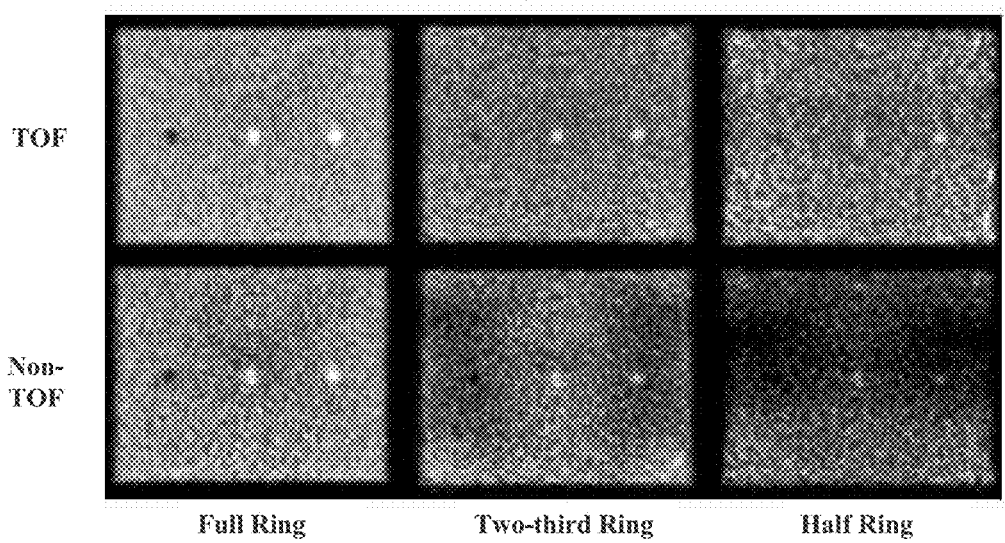
FIG. 5 provides cranio-caudal views of reconstructed images for three different scanner designs (1-mm spatial resolution).

In some embodiments, the detector array occupies about 50% of the space defining the ring around the imaging situs. In other embodiments, the detector array occupies about ⅔ of the space defining the ring around the imaging situs. In recent work it has been shown that the number of angular views necessary for an artifact-free image reconstruction is reduced as timing resolution improves (47). In that work, data projections were summed into coarser angular views in a regular pattern, while still sampling the full angular FOV in the scanner. Pursuant to the present invention, it was of interest to evaluate the impact TOF information has in reconstructing data with an irregular pattern of missing projections. Simulations for a breast scanner design were performed in order to understand the benefit of TOF in reconstruction of such limited angle PET data sets. In particular the trade-off between timing resolution and the limited angle coverage, as well as image artifacts, was investigated. The simulated scanner had a ring diameter of 15-cm and axial length of about 15-cm. Different LSO crystal sizes were investigated, leading to reconstructed spatial resolutions of 1, 2, and 3-mm respectively. For these simulations the crystal length was fixed at 10-mm. The simulated phantom was a 10-cm diameter by 8-cm long cylinder containing three 5-mm diameter hot lesions with 8:1 uptake with respect to background, and one cold lesion. Image reconstruction was performed using data from a full scanner ring, a two-third scanner ring, and a half scanner ring: FIG. 4 depicts the setup of three simulated scanner designs: a full ring (B), a two-third ring (120° in-plane angular coverage) (C), and a half ring (90° in-plane angular coverage) (D). The ring diameter of the scanner was 15-cm. The simulated phantom (A) was a 10-cm diameter× 8-cm long cylinder, that contained three 5-mm diameter hot lesions (1, 2, 3) and a cold 5-mm diameter lesion (4). FIG. 5 shows reconstructed cranio-caudal images for the full and partial ring breast scanner setups without and with TOF information (timing resolution of 200 ps and 1-mm spatial resolution). The Non-TOF scanner has significant non-uniformities in the image as the number of angular views is reduced, leading to limitations in lesion detection and quantification. Improved localization of the annihilation points along the LORs, due to better timing resolution in the TOF scanner, leads to very few signs of non-uniformity. Initial results therefore showed that for Non-TOF imaging only a full ring scanner gives acceptable images, while with TOF imaging a two-third ring scanner can also produce clinically useful images that are as good as the full ring Non-TOF images.

Various detector scintillator designs may be used in accordance with the present invention. The detector array may comprise scintillator crystals of NaI(Tl), lutetium oxyorthosilicate, lutetium yttrium oxyorthosilicate, gadolinium orthosilicate, or lanthanum bromide. Any suitable scintillator crystal may be used, and various other crystal types will be readily recognized among persons of ordinary skill in the art. Each of the crystals in a detector may have a length of about 10 to about 30 mm. Each of the crystals have an individual size of 4×6×20 mm$^3$, or may have an individual size of 2×2×10 mm$^3$. One or more surfaces of each of the crystals may be polished or unpolished, with polished surfaces being preferred.

Early timing measurements with LaBr$_3$ scintillators were carried out in parallel with similar measurements on LYSO scintillators. Some of these results with LYSO crystals are summarized in Table 1, below. Table 1 shows coincidence timing resolution measurements with single LYSO crystals on a Hamamatsu H4998 PMT, and results from the Philips Gemini TF PET/CT scanner system timing resolution. The Gemini scanner uses an Anger-logic detector design with 4×4×22 mm$^3$ LYSO crystals and a PMT that does not have timing properties as good as the H4998. All measurements were in coincidence with the same type of detector as the one being investigated.

TABLE 1

| Measurement | LSO/LYSO Δt (fwhm) |
| --- | --- |
| Small 2 × 2 × 10-mm$^3$ single pixel | 300 ps |
| 4 × 6 × 25-mm$^3$ single pixel | 250 ps |
| Gemini scanner | 585 ps |

In particular, such measurements demonstrate that with a fast PMT, it is possible to obtain a coincidence timing resolution of 300 ps with a small 2×2×10-mm$^3$ LYSO (5% Yt) pixel.

Besides measurements with single crystals placed directly on a PMT, pixilated Anger-logic detectors were also developed herein, such detectors being similar in concept to Non-TOF detectors that were built previously with GSO (17) and NaI(Tl) (61). The use of a continuous lightguide coupled to the crystal array extends the performance of the traditional continuous Anger-logic detector by controlling the spread of light in a thick detector to achieve better spatial resolution and count-rate capability. The advantage of this detector compared to a block detector (18, 19) is that the light collection is significantly more uniform for all crystals in the array, thereby leading to better energy and timing resolution throughout the detector. A consequence of these measurements has been the development of a commercial TOF PET scanner for clinical imaging (e.g., Philips Gemini TF PET/CT) (46) with a system timing resolution of 585 ps with detector arrays composed of 4×4×22 mm$^3$ LYSO crystals. Using a faster timing PMT such as the Hamamatsu H4998 can lower the coincidence timing resolution to about 400 ps in this detector (62), while improved timing electronics such as those developed herein (see Example 5, infra) (45, 63) can potentially reduce the timing resolution further (<400 ps), bringing it closer to the single crystal measurements. Hence, the coincidence timing resolution of 300 ps measured with a small 2×2×10-mm$^3$ LYSO (5% Yt) pixel can be maintained, without significant degradation, in the present pixelated Anger-logic detector design with an appropriate choice of PMT and fast, accurate timing electronics, as described more fully infra.

Each of the at least two segments of the detector array may be coupled to a photodetector array. Each segment may be coupled to a photodetector array via a continuous lightguide, or may be coupled to a photodetector array without an intervening lightguide. The photodetector array may be a photomultiplier tube. The photodetector array may comprise single-channel photomultiplier tubes, multi-anode photomultiplier tubes, position sensitive multiplier tubes, or silicon photomultiplier tubes. Those skilled in the art may readily identify suitable single-channel photomultiplier tubes, multi-anode photomultiplier tubes, position sensitive multiplier tubes, and silicon photomultiplier tubes.

In order to provide discrimination of 2×2 mm$^2$ cross-section crystals in an Anger-logic detector design, a modified pixelated Anger-logic detector has been developed using small crystals read out by an array of either small photomultiplier tubes (PMTs) or multi-anode PMTs (MAPMT) (17). Such a detector was successfully designed in the past for discriminating 2×2×10 mm$^3$ GSO and LYSO crystals using an array of 19-mm diameter PMTs (21). This detector was implemented in a small animal PET scanner (APET) (21, 22), which was also commercialized as the MOSAIC animal scanner by Philips Medical Systems. The basic detector involves an array of crystals that is coupled through a lightguide to a continuous array of PMTs. An advantage of this design is the uniform light collection for all crystals, leading to good crystal discrimination as well as energy and timing resolution.

In modern PET scanners based on pixelated detectors a common technique is to use Anger-logic positioning with encoding of the crystal to a PMT (17, 18, 64). As a calibration step, boundaries are drawn between all individual crystals in a flood map and a look-up table generated which assigns all events within a region (region-of-interest, ROI) to the center position of that crystal (see FIGS. 6A-6B). The center position is the real physical position of that crystal on the scanner surface. FIG. 6B shows schematically the crystal space partitioned into ROIs where all points within each ROI are located closest to that ROI peak. Simulations were performed for a pixelated detector where only the γ-ray interactions are tracked and the interaction position is calculated as an energy-weighted mean of the γ-ray interaction points. The γ-ray entry points were uniformly distributed over a single crystal surface area. The energy-weighted interaction position of the γ-rays was then mapped onto a 2D array of regions-of-interest (ROI), each of which was either equal or half the size of a crystal. The results showed that using half size ROIs leads to a reduced error in positioning of the γ-ray entry point (defined as the difference between the measured position and the true entry point of the γ-ray) for Compton scattered events.

Figure 6:
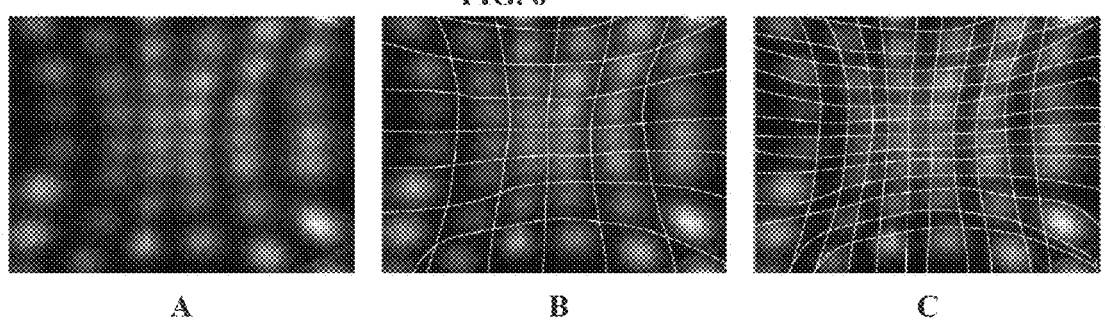
FIG. 6 shows a schematic picture of drawing regions around individual crystals during crystal calibrations.

FIG. 6 provides a schematic picture of drawing regions around individual crystals during crystal calibrations. FIG.

6A is a flood map over a portion of a single PMT region showing events within individual crystal. FIG. 6B depicts a standard calibration technique; all measured events are placed at the physical center (crystal position on the scanner) of an ROI. The ROI regions are centered over individual crystals and are the same size as the crystal pitch. FIG. 6C shows an inter-crystal positioning technique; all measured events are placed at the physical center of an ROI (every half crystal position on the scanner). The ROI regions are centered over individual crystals and are of size that is half the crystal pitch leading to four times the number of ROIs as in the standard calibration technique.

Based upon these results, an inter-crystal positioning technique (as in FIG. 6C) was evaluated to reduce the impact of detector Compton scatter in the reconstructed spatial resolution of the scanner. In this technique, all measured events are still placed at the physical center of an ROI. However, the ROIs are centered over individual crystals but are half the size as the crystal pitch, with one additional (inter-crystal) ROI sampling the region between adjacent crystals. Events within each ROI centered over a crystal are still placed at the physical position of that crystal on the scanner. However, those events which lie within each inter-crystal ROI are now placed at a physical position which is in the middle of adjacent real crystal positions. This leads to a doubling (half the crystal pitch) of the detector sampling rate and potentially better sampling of Compton scattered events which are now also placed at positions lying in between those crystals. In addition, by essentially sampling every half-crystal pitch, there will be some gain in spatial resolution due to improved sampling of the detector point spread function (PSF). The improved PSF sampling with the inter-crystal technique also has an advantage over the past "wobbling" methods since it does not involve any mechanical motion of the detectors. The technique was tested on the APET scanner and measurements showed that the transverse spatial resolution for a point source near the center of scanner improved from 1.9-mm to 1.6-mm. This technique is used in the present design to achieve high spatial resolution.

An important factor determining the sensitivity of a scanner is the crystal stopping power as well as the crystal thickness used in the detector. Table 2, below, summarizes the coincidence stopping efficiency at 511-keV for LSO scintillator as a function of crystal thickness. For comparison, the crystal coincidence efficiency in a current BPET scanner is 8.5% (19-mm thick NaI(Tl)). A 10-mm thick LSO crystal will intrinsically double the sensitivity of this scanner without a change in geometry, while a 15-mm thick LSO crystal will quadruple the intrinsic sensitivity.

TABLE 2

| | Crystal thickness (mm) | | | | |
|---|---|---|---|---|---|
| | 10 | 15 | 20 | 25 | 30 |
| LSO coincidence efficiency (%) | 17.0 | 34.0 | 45.3 | 59.1 | 66.2 |

Scanner sensitivity can also be increased by reducing the scanner ring diameter and thus covering a larger solid angle. Both these options for increased sensitivity, however, lead to an increased parallax effect in the detector, which requires a depth-of-interaction (DOI) measurement to reduce degradation in spatial resolution as a function of radial position in the scanner. An important design trade-off that has been considered in the present simulations is the relative impact of parallax effect as a function of crystal thickness and sensitivity on lesion detection and quantification tasks.

EXAMPLES

Example 1

Impact of Spatial and Timing Resolution in Dedicated Breast Scanner

Figure 7:
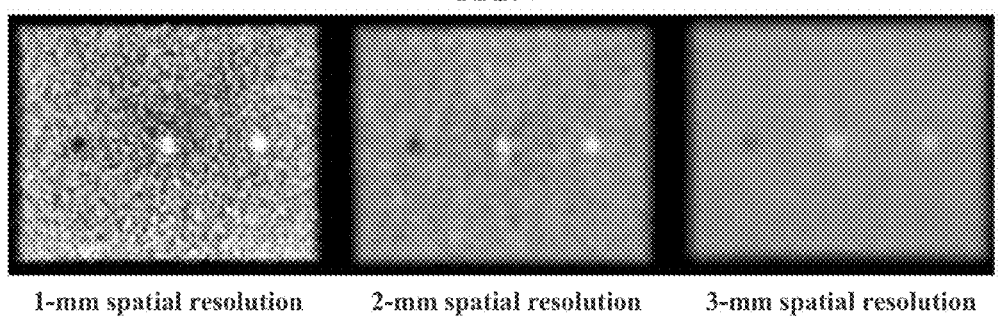
FIG. 7 shows reconstructed images from simulations of the lesion phantom in a full ring scanner design.

Because breast imaging involves detection and quantification of small lesions with low activity uptake relative to the background, the scanner spatial resolution can have a significant effect on the resultant images as well as the measured lesion uptake. FIG. 7 shows reconstructed images from simulations of the lesion phantom in a full ring scanner design as shown in FIG. 4B. The lesions are 5-mm in diameter with an 8:1 uptake (for hot lesions) relative to the background. The images are shown for the three different spatial resolutions that were simulated. Since the full ring scanner does not suffer from image artifacts, only images for the Non-TOF reconstruction are shown. As can be seen, the lesions appear sharper as the crystal cross-section is reduced, implying that improved contrast is achieved with the smaller crystals. Visually, the images show that while a spatial resolution of 1-mm produces high quality images and 2-mm resolution is also adequate for detecting and quantifying the small 5-mm diameter lesions, 3-mm spatial resolution significantly limits the scanner capabilities. Hence, the goal in the present design was to achieve a reconstructed spatial resolution in the range of 1-2-mm.

For a quantitative comparison, the measured contrast recovery coefficient (CRC) was calculated for the three hot lesions. The CRC was measured in a manner analogous to that prescribed in NEMA NU2-2001 (65). Regions-of-interest (ROIs) were drawn over spheres, equal in size to the sphere diameters, to obtain the mean counts ($C_H$ for the hot, and $C_C$ for the cold lesion) Annular regions beyond the sphere diameter were drawn to estimate the background counts ($C_B$). The background ROIs were drawn locally in this manner due to the non-uniformities and artifacts which arise in some of the reconstructed images for partial ring scanner geometries that will lead to an incorrect estimation of the background counts. CRC for hot spheres was calculated using the NEMA definition (65):

$$CRC = \frac{\frac{C_H}{C_B} - 1}{8 - 1} \quad (1)$$

Similarly, for the cold sphere, CRC was estimated by:

$$CRC = 1 - \frac{C_C}{C_B} \quad (2)$$

Figure 8:
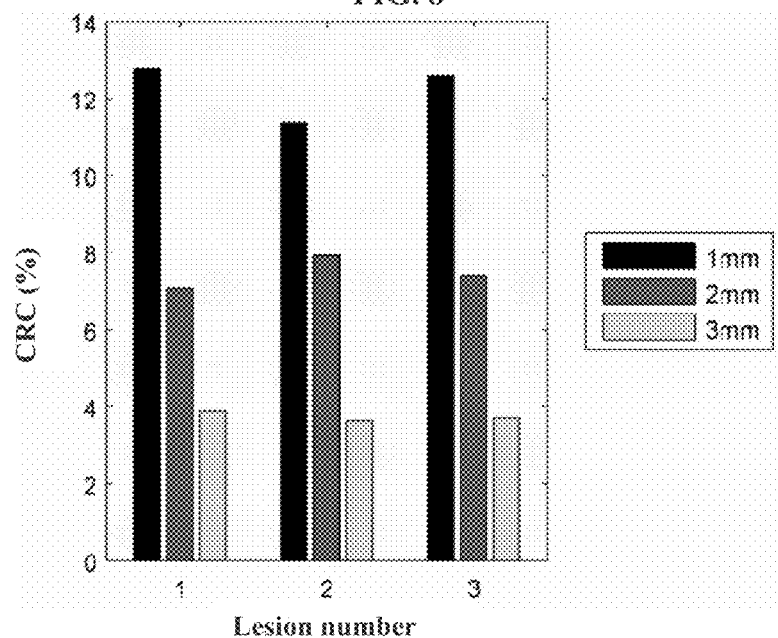
FIG. 8 provides the measured CRC values for the three 5-mm diameter hot lesions in a full (complete) ring Non-TOF scanner with three different spatial resolution values of 1-mm, 2-mm, and 3-mm.

FIG. 8 shows the results for the three hot lesions. As the spatial resolution improves, there is a noticeable gain in CRC values for these lesions due to improved spatial resolution. A similar trend was observed for the cold lesion (Lesion 4) where the CRC values were 46%, 35%, and 16% for spatial resolutions of 1-mm, 2-mm, and 3-mm, respectively. From these results it is very clear that spatial resolution has a significant impact on the quantification capability of the breast scanner for small lesions and for a successful design the spatial resolution should be <2 mm. It is important to note that the latest clinical PET scanners with spatial resolution values in the range of 4-6 mm will not be useful in detection or quantifying these small lesions (<5 mm in diameter) with similar uptake levels.

Figure 9:
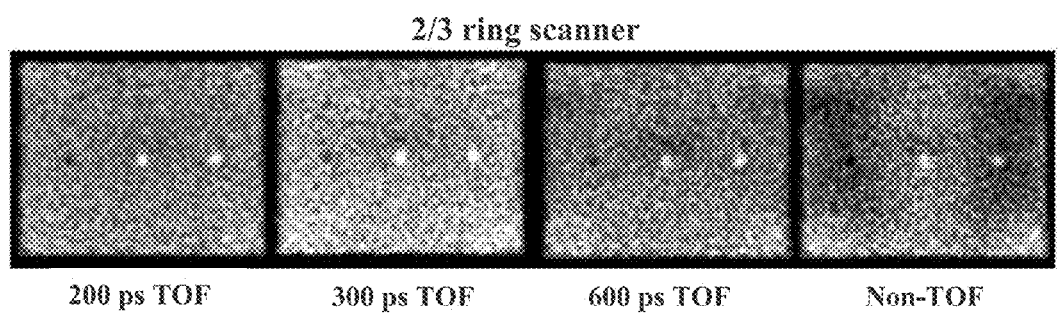
FIG. 9 shows the central cranio-caudal slices for the reconstructed images from a two-third ring scanner as a function of timing resolution (scanner spatial resolution of 1-mm).

For a qualitative comparison of the impact of timing resolution and angular coverage in the scanner on the resultant images, FIG. 9 shows the central cranio-caudal slices for the reconstructed images from a two-third ring scanner as a function of timing resolution (scanner spatial resolution of 1-mm). The four images moving left to right are: 200 ps TOF, 300 ps TOF, 600 ps TOF, and Non-TOF. Note that the lesions are 5-mm in diameter with an 8:1 uptake (for hot lesions) relative to the background and all images are from simulated data. The Non-TOF image has significant artifacts that make it not very useful for quantifying small lesions. With 600 ps and better timing resolution the TOF reconstructed images from the two-third ring scanner are all artifact-free. While the 600 ps image seems adequate, the 300 ps image appears qualitatively much better and represents the type of image desired for a breast scanner design.

Figure 10:
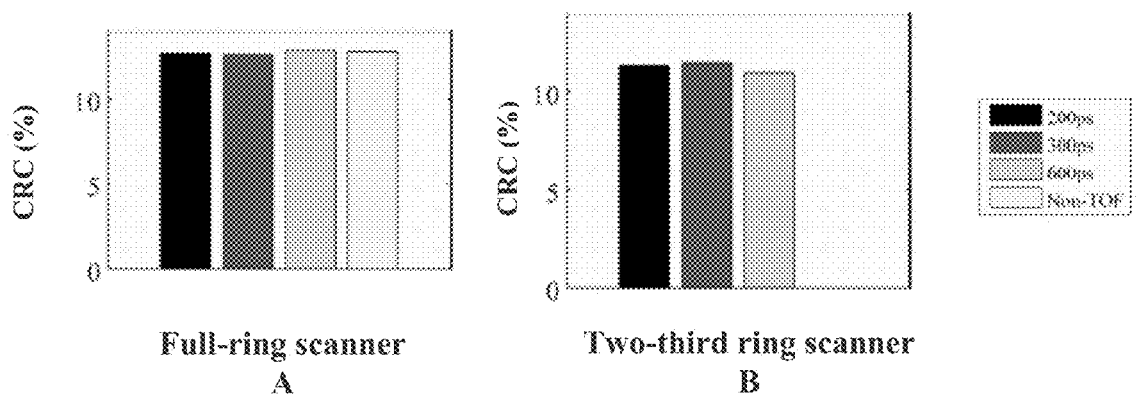
FIG. 10 provides the CRC values for a 5-mm diameter 1 lesion in a 10-cm diameter phantom for a Full ring (A) and two-third ring (B) scanner for 200 ps TOF, 300 ps TOF, 600 ps TOF, and Non-TOF reconstructions.

FIG. 10 shows the measured CRC values for a hot lesion (Lesion 1) in the Full and two-third ring scanners as a function of timing resolution. The results are shown only for those images that were deemed to be relatively artifact-free for analysis. The results show that TOF imaging has no impact on the CRC values achieved in the Full ring scanner. For the two-third ring scanner, a timing resolution of 600 ps or better leads to CRC values which are similar to those achieved in the Full ring scanner.

Example 2

Design and Intrinsic Performance of a Dedicated Breast Scanner (BPET)

In the past, a continuous NaI(Tl) based breast scanner (BPET) was developed which performed an iterative, limited angle, image reconstruction, and was used for pilot clinical studies (40-42). This scanner includes two 19-mm thick, continuous, curve-plate NaI(Tl) detectors with 28×21-cm² surface area (FIG. 11A) and signal readout performed by an array of 39-mm diameter PMTs. The BPET scanner was designed for a woman to lie prone on a thin table with the detectors lying directly underneath (FIG. 11B). A ¼-inch lead shielding was added under the tabletop in order to shield the detectors from out-of-field activity in the body. The energy resolution of this scanner was 10% at 511 keV leading to good scatter rejection with an energy gate set above 425 keV. The measured spatial resolution was 3.8-mm at the center of the scanner and which changes to 4.5-mm at radial distance of 5-cm due to parallax effects.

Figure 12:
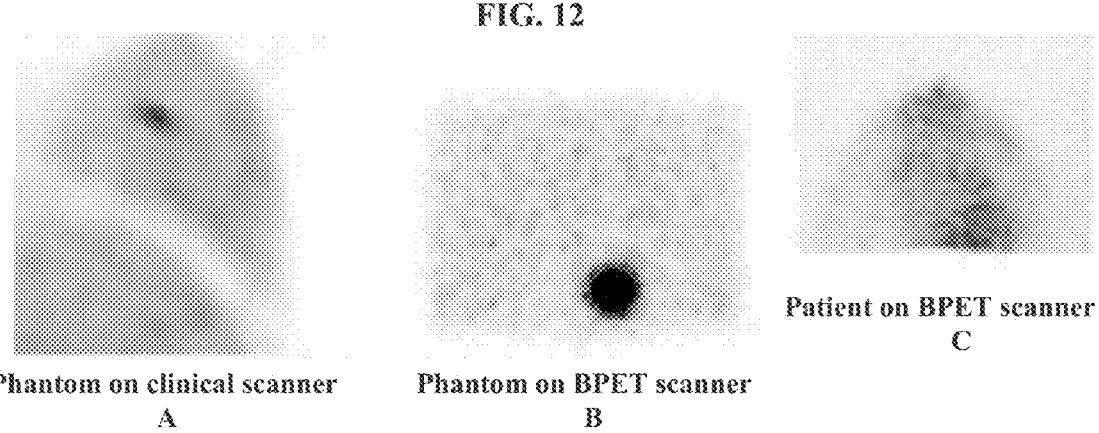
FIG. 12 provides images from breast a phantom study with a 1-cc lesion (10:1 uptake relative to background) in (A) the whole-body Allegro and (B) dedicated breast BPET scanner. The phantom used in Allegro study was a Data Spectrum breast attachment (10-cm diameter breast) to an anthropomorphic body cavity scanned in a prone position. The phantom used in the BPET study is a 10-cm diameter cylinder. (C) Image of the left breast in a patient scanned on the BPET scanner.

FIGS. 12A-C show reconstructed images from a breast phantom study with a 1-cc lesion (1.2-cm diameter and 10:1 activity uptake with respect to background). FIG. 12A shows images from the wholebody Philips Allegro PET scanner (52) where a breast phantom was scanned from Data Spectrum that uses a breast attachment to the anthropomorphic body cavity. This study simulated a prone scanning orientation for a patient study in a whole-body scanner. The 1-cc lesion was placed in one breast compartment and the data were reconstructed in 4-mm voxel space as shown in FIG. 12A. Since the breast attachment from Data Spectrum uses a rigid plexiglass base to attach to the anthropomorphic body cavity, it was not feasible to use this attachment for imaging in the BPET. Instead we scanned the 1-cc lesion in a 10-cm diameter cylindrical phantom placed within the BPET FOV to mimic the same phantom diameter, lesion size, and lesion uptake (10:1 with respect to background) as that used in the whole-body scan. FIG. 12B shows the reconstructed image (1-mm voxels) from the BPET scan. By drawing circular ROIs around the lesion and in the background we measured uptake ratios of 7:1 and 3:1 in the BPET and Allegro images, respectively.

This phantom study demonstrated the higher uptake achieved with BPET scanner, indicating the potential for improved quantification of small lesions in the BPET scanner. Subsequently, pilot human studies have also been performed with the BPET scanner. FIG. 12C show the reconstructed BPET image for a patient injected with 10-mCi of $^{18}$F-FDG and scanned about 2 hours after injection. The BPET image shows a complex lesion in this breast with a "hot" focus surrounded by a diffuse pattern of uptake. One month later, pathology after mastectomy confirmed the imaging findings with a 3.5-cm invasive ductal carcinoma within an 8-cm region of high grade DCIS. The images from this pilot study also reinforce the notion that nonspecific uptake of $^{18}$F-FDG in the breast leads to reduced efficacy of $^{18}$F-FDG PET imaging. However, development of new, more specific tracers, together with improved PET instrumentation, can provide new directions for PET imaging in breast cancer.

The moderate spatial resolution and sensitivity of the BPET scanner do, however, limit its use for quantifying small, early stage breast tumors. In addition, due to the nature of Anger positioning with large 39-mm diameter PMTs, spatial resolution is limited near the detector edge. This leads to a 2-cm detector dead area at the top of the detector (near the table), which limits its ability to image lesions close to the chest wall. The present design aimed to overcome these limitations, while using the experience gained with BPET imaging studies to develop a high performance breast scanner.

Example 3

Design a High Sensitivity and Spatial Resolution Detector with TOF Capability

The LYSO-based detector developed for the APET scanner provides (21, 22) a 1.6-mm reconstructed spatial resolution (with inter-crystal positioning) and detector coincidence sensitivity of 17% (10-mm thick crystal in Table 2, above). In addition, the intrinsic coincidence timing resolution of the 2×2×10-mm³ LYSO crystal used in that detector is 300 ps (Table 1) that makes it a practical design for use in a dedicated TOF breast scanner. For improved spatial resolution (better than 1.6-mm) crystals with cross-sections smaller than 2×2-mm² were evaluated, while for higher scanner sensitivity crystals thicker than 10-mm were investigated. Smaller and/or longer crystals, however, adversely affect the scintillation light collection process, leading to possible degradations in energy and timing resolution especially as a function of DOI (66). The present example involved the investigation and benchmark of the energy and timing resolutions of 10-20 mm long and 1.5×1.5-2×2-mm² cross-section LYSO crystals with different surface finish. Special attention was paid to the impact of DOI on the energy and timing resolutions. Subsequently, pixelated Anger-logic detector arrays were developed for use in the breast scanner with inter-crystal positioning for improved spatial resolution.

Experimental Setup.

Figure 13:
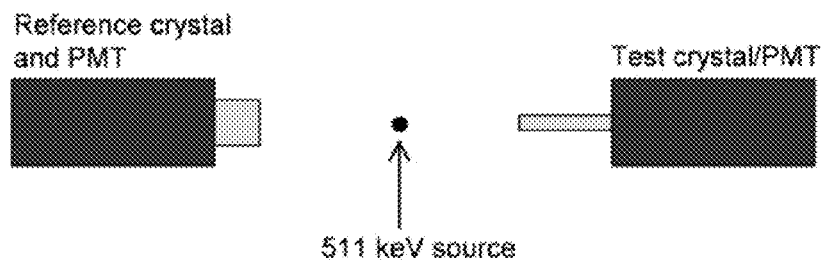
FIG. 13 depicts a schematic showing a top view of the measurement setup for a standard crystal/PMT coincidence measurement. The reference crystal is $LaBr_3$ (5% Ce) placed on a fast Hamamatsu H4998 PMT.

The general experimental setup for measurements is as shown FIG. 13. The measurements were performed in coincidence with a fast reference detector that provides the trigger start time for the electronics. A LaBr$_3$ (5% Ce) crystal on a Hamamatsu H4998 PMT were used for this reference detector. The test detector was coupled to either another Hamamatsu H4998 PMT for crystal measurements, or a new PMT under evaluation.

Detailed Methods. (a) Optimization of Crystal Size and Surface Finish:

For improved spatial resolution and sensitivity small and long crystals, respectively, are needed. The crystal cross-section and length, both of which determine the number of reflections undergone by scintillation photons, therefore affect the measured energy and timing resolutions. Crystal surface finish also plays a very important role in terms of scintillation light collection in the crystal and can have an affect on the final energy and timing resolution achieved in small, long crystals. Initial measurements were performed with a 2×2×10 mm³ and a 4×6×20 mm³ LYSO crystal. All crystal surfaces were polished and the crystals were wrapped on all five sides that are not coupled to the PMT in several layers of Teflon paper. In addition, another 4×6×20 mm³ LYSO crystal was tested with the four long surfaces having a diffuse finish. Measurements for energy and coincidence timing resolution are shown in Table 3, below. The coincidence timing resolution for both crystal sizes with polished surfaces is good for TOF imaging capability. With diffuse surface there is, however, a significant degradation in the coincidence timing resolution for the 4×6×20-mm³ crystal.

TABLE 3

| Crystal size (mm³) | Surface finish | Energy resolution at 511-keV (%) | Coincidence timing resolution (ps) |
|---|---|---|---|
| 2 × 2 × 10 | Polished | 13 | 300 |
| 4 × 6 × 20 | Polished | 12 | 250 |
| 4 × 6 × 20 | Diffuse | — | 1030 |

Figure 14:
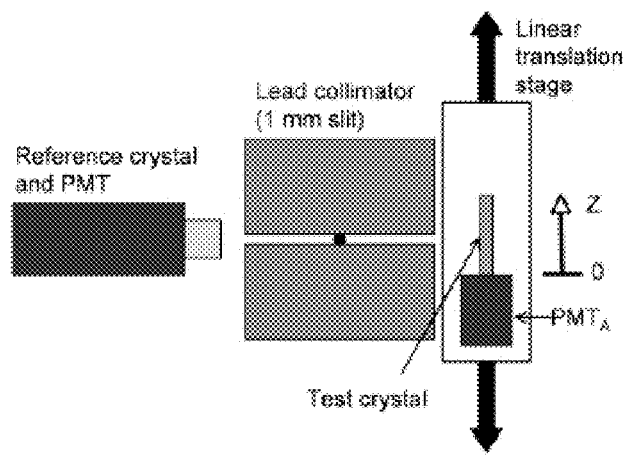
FIG. 14 provides a schematic showing a top view of the measurement setup for studying the impact of DOI on energy and timing resolution. The test crystal and the PMTs are on a linear translation stage that moves perpendicular to the 511-keV photon beam which is collimated by a 1-mm slit in a lead collimator. The reference crystal and PMT are used for coincidence measurements for timing data.

To better understand the various factors affecting the timing resolution in small and long scintillators, additional measurements were set up for timing as a function of DOI (setup as shown in FIG. 14). The 4×6×20 mm³ LYSO crystals with two different surface finishes (polished and diffuse) were investigated in coincidence with a small LaBr$_3$ (5% Ce) placed on an XP20D0 PMT.

Figure 15:
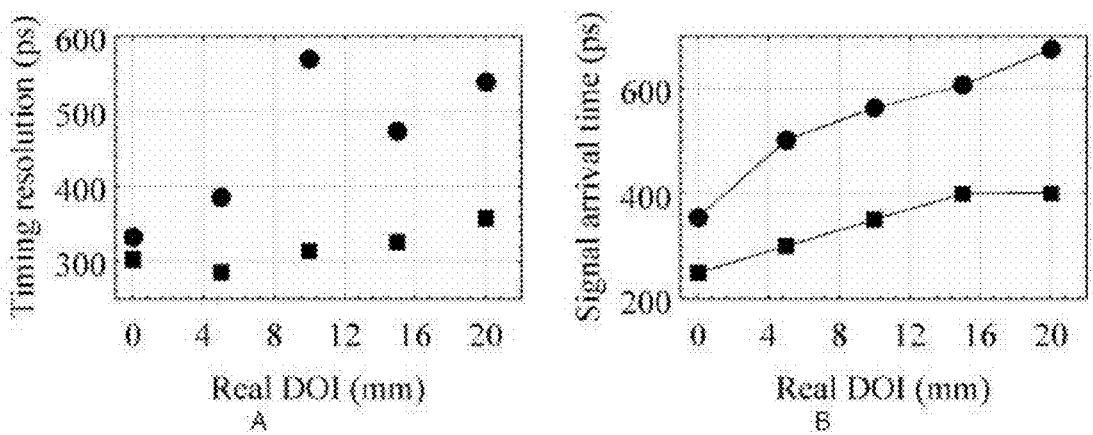
FIG. 15 shows the (A) Measured timing resolution and (B) signal arrival time for signals from $PMT_A$ (see FIG. 16) as a function of incident position (real DOI) along the crystal length. The numbers are for measurements performed in coincidence with a small $LaBr_3$ (5% Ce) placed on an XP20D0 PMT. The crystals are 4×6×20 mm³ LYSO crystals, one having all surfaces polished (■), while the other has a diffuse finish on its four long surfaces (●). A real DOI position of 0-mm corresponds to the crystal edge coupled to $PMT_A$.

In FIG. 15, the signal arrival time is plotted against the timing resolution for the two crystals as a function of interaction point in the crystal. For these measurements a real DOI position of 0-mm corresponds to the crystal edge coupled to PMT$_A$. The coincidence timing resolution numbers (FIG. 15A) show some variation as a function of DOI in the diffuse crystal but are fairly constant in the polished crystal. This may be due to the additional reflections undergone by the first few scintillation photons in the diffuse crystal that will affect the initial rise time of the signal as the interaction point (real DOI) moves further away from the PMT.

Also, FIG. 15B shows a constant change in the signal arrival time (centroid of the timing histogram) as the distance from PMT increases. Without any corrections, this change in signal arrival time as a function of DOI will lead to a degradation in the timing resolution of the detector. There are two effects that account for this systematic shift in the arrival times. First, the distance traveled by scintillation photons further away from the PMT is larger, leading to a delayed signal arrival time at the PMT surface. This effect can in practice be reduced by performing a DOI dependent calibration on the measured signal arrival time and will only be possible in a DOI measuring detector that we are not proposing in this project. However, for a 20-mm long crystal this effect leads to about a 50 ps difference between events at opposite ends of the crystal (time difference=(n−1)*L/c, where n the index of refraction of 1.82, L is crystal length, and c is the speed of light in vacuum) (66). Convolving the Gaussian distribution (fwhm=250 ps) of timing histogram with interaction depth probability in the LSO crystal (e−µl where µ is the linear attenuation coefficient of LSO and, l is the DOI along the crystal) leads to a degradation in timing resolution to about 260 ps, which is not a significant effect.

The second effect causing the shift in signal arrival time is due to a time "slewing" effect arising due to smaller signal amplitude for events located farther away from the PMT. This effect also causes some degradation in the intrinsic timing resolution due to a reduced statistical quality of the signal. A correction for this time slewing is needed and requires correlating the collected charge (integrated signal or energy) with the pickoff time at several points along the signal rise time. A similar technique was successfully implemented for the CDF (Collider Detector Facility at Fermilab) (67) TOF system by the HEP engineering group at the University of Pennsylvania, and will be a part of the flexible signal processing techniques being developed for use in the electronics for this project. The measurements performed with the smaller crystal sizes evaluate these effects to accurately correct for the variation in timing resolution. However, measurements already show that a good timing resolution of 300 ps in a 2×2×10-mm3 LYSO crystal can be achieved without any DOI-dependent corrections.

For this project several LYSO crystals were tested that are 10-20 mm long and 1.5×1.5-2×2 mm² in cross-section. In addition, different crystal surface finishes were investigated. These choices allow the development of detectors with spatial resolution in the range of <1.6-mm (with inter-crystal positioning) and high sensitivity. The general experimental setup for these measurements will be the same as shown earlier in FIGS. 13 and 14 with the aim being to benchmark the overall energy and timing resolutions.

Choice of Photomultiplier Tube (PMT):

The main variables in the design of this detector will be the choice of either a fast single channel PMT with appropriate size for achieving good discrimination of small crystals or a multi-anode PMT (MAPMT). Previous work with the development of the APET animal scanner showed that the 19-mm diameter R1450 PMTs produced good discrimination of 2×2-mm2 cross-section crystals. This PMT also has a fast rise time (1.8 ns) making it suitable for use in a TOF PET detector (68). Similar or smaller size PMTs with fast rise times may be used in order to discriminate equal or smaller size crystals while achieving good timing resolution as well. Several fast PMTs of sizes similar or smaller than the R1450 were investigated. Table 4, below, lists the important timing characteristics of three such single-channel PMTs currently available from Hamamatsu, as well as a multi-anode PMT, that will be evaluated for their timing and energy response before being used in some embodiments of the instant detector design.

TABLE 4

|  | XP20D0 | R1450 | R4124 | R4868 | H8500 |
|---|---|---|---|---|---|
| Diameter (mm) | 51 | 19 | 13 | 10 | 52 (square), anode pitch 6.3 |
| Multi-channel | No | No | No | No | Yes (64 channels) |
| Rise time (ns) | 1.5 | 1.8. | 1.1 | 1.0 | 0.8 |
| Transit time spread (ns) | 0.6 | 0.76 | 0.5 | 0.7 | 0.4 |
| QE at 420 nm (%) | N/A | 25 | 25 | N/A | 24/33 |

All of these PMTs have peak sensitivity in the visible light range. For comparison purposes, the Photonis XP20D0, which is currently the standard PMT used for timing measurements, is also included. The three single channel PMTs from Hamamatsu have comparable timing characteristics to the standard XP20D0 PMT, while the H8500 MAPMT has seemingly even better timing characteristics.

However, dispersion in the gains of the 64 channels can lead to a degradation in timing performance if proper corrections are not included. In spite of this limitation, it has recently been shown (69) that a coincidence timing resolution of 370 ps can be obtained with this PMT and a 2.9×2.9×20 mm$^3$ LSO crystal without any such corrections. Measurements were made using a single 2×2×10 mm$^3$ polished LYSO crystal coupled to this MAPMT and placed directly over different anodes (total of 64).

Results show a measured coincidence timing resolution of 300-400 ps, with the variation in numbers arising due to the different gains of the individual anodes. It is believed that a proper alignment of the varying gains between different anode channels, and an increased QE in a newer version of this MAPMT (70), will lead to a higher performance fast PMT for use in the present detectors. As will be recognized among those having ordinary skill in the art, energy and timing resolution measurements may be performed to choose either a reasonable size single-channel PMT or the H8500 MAPMT, which is believed to be able to provide good performance in a pixelated Anger-logic detector.

Develop a Pixelated, TOF, Anger-Logic Detector.

Figure 16:
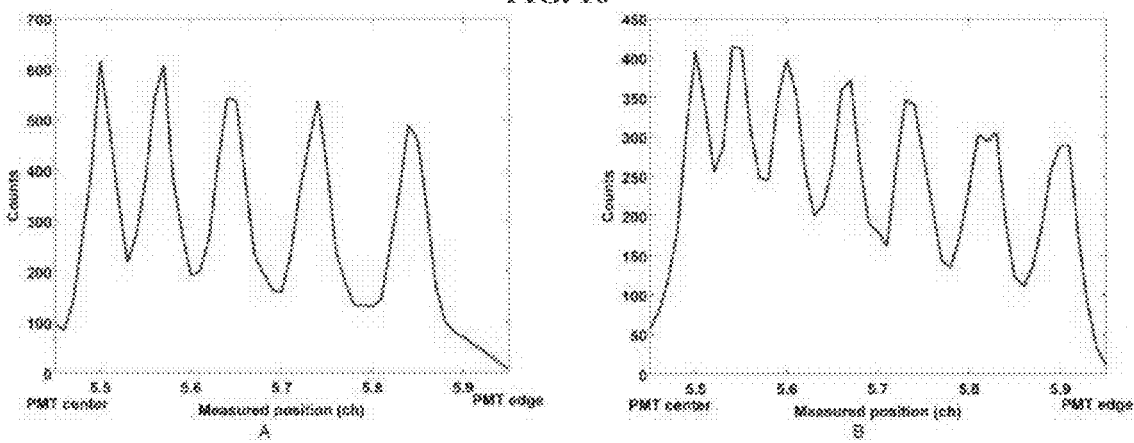
FIG. 16A provides a profile from a simulated flood image for a 2×2×20 mm³ LYSO crystal based pixelated Anger-logic detector read out by an array of 19-mm diameter PMTs.
FIG. 16B shows a profile from a simulated flood image for a 1×1×20 mm³ LYSO crystal based pixilated Anger-logic detector read out by an array of 13-mm diameter PMTs.

Montecrystal detector simulation (17, 53) may be used successfully to optimize the lightguide design for discrimination of small crystals using relatively large PMTs. For the present invention, the simulations are used as a guide for bench-top measurements. FIG. 16A shows simulated images for crystal discrimination in a pixelated Anger-logic detector using 2×2×20 mm$^3$ LYSO crystals readout by an array of 19-mm diameter PMTs (same as the APET detector). A clear separation of the crystals is achieved in this setup. Based upon these simulations the detector for the small animal APET scanner was developed, and the measured flood images show that the simulations accurately predicted the ability to design this detector using an appropriate size PMT and lightguide thickness. In moving forward towards a detector for our breast scanner design, initial detector simulations were performed for discrimination of 1×1×20 mm$^3$ LYSO crystals readout by an array of 13-mm diameter PMTs. The simulated crystal discrimination profile is shown in FIG. 16B. The seven crystals spanning half a PMT diameter region are well discriminated, though a smaller PMT or a MAPMT will produce better results. It is important to point out that these simulations (Montecrystal) account for all physical effects in the detector, i.e., Compton scatter, scintillation light emission and spread, crystal surface finish, and scintillation light reflections within the detector.

Figure 17:
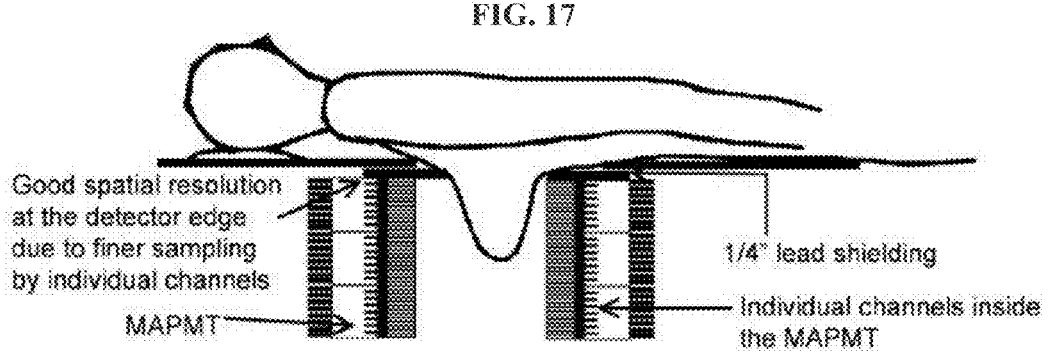
FIG. 17 is a schematic view of a woman lying prone on the BPET scanner table with the breast lying between two detectors using MAPMTs as the photo-detectors. As shown, there are eight channels within each MAPMT (1D view) which provides good spatial resolution close to the detector edge and the patient chest wall.

For improved crystal discrimination a multi-anode PMT (MAPMT) may also be used. The Hamamatsu H8500 MAPMT includes an 8×8 array of multiple anodes with an anode pitch of about 6.3-mm. The fine anode pitch of this MAPMT will allow a high sampling of the scintillation light in the Anger-logic detector, leading to good crystal discrimination and spatial resolution all the way to the detector edge. FIG. 17 shows a schematic of this design with the female patient lying chest-downwards on the current BPET bed. The fine pitch of the MAPMT channels will allow discrimination of crystals very close to the edge since the dead area will now be about half the anode pitch (≈3 mm) as opposed to 2 cm in the original BPET design which uses 39-mm diameter PMTs.

This greatly improves imaging capability near the patient chest wall that was a limitation in the earlier BPET design. In addition, for this MAPMT it is also possible to multiplex the multiple anodes at the center of the detector into 2×2 arrays, leading to an effective anode pitch of 12.6-mm. This will reduce the complexity of the scanner in the central detector regions by having a smaller number of electronic channels and triggers, without significantly affecting the spatial resolution (see simulated crystal discrimination with 13-mm diameter PMTs in FIG. 16B).

Based upon the results from investigations above, those skilled in the art will recognize that the simulation may be used to design an appropriate lightguide for discrimination of small crystals (1.5×1.5 mm$^2$ and 2×2 mm$^2$ cross-section) using a fast single channel PMT or a multi-anode PMT. Small detector arrays (equivalent to about half a PMT area) may also be constructed to perform detector array measurements for energy and timing resolution, as well as crystal discrimination, to benchmark the detector performance.

Impact of Inter-Crystal Positioning on Resultant Images.

Phantom measurements are performed on an LYSO-based APET scanner. This scanner has a ring diameter of about 20-cm. Design of a cylindrical phantom may be arranged similarly to that shown in FIG. 4A to evaluate the impact on the CRC value for hot and cold lesions with and without inter-crystal positioning. Based upon measured point source spatial resolution (spatial resolution of 1.6-mm) improved CRC values may be seen with the use of inter-crystal positioning technique, which will lead to improved lesion detectability as well. Measurements are performed as a function of count statistics and object size. This is done to evaluate improvements in CRC due to better spatial resolution as function of noise in the image (related to collected count density). For low count density in the image, the precision of the improved CRC will be low, leading to a potentially reduced impact of the improved spatial resolution.

Measurements on the APET scanner clearly indicate the ability to achieve a reconstructed spatial resolution of 1.6-mm with the pixelated Anger-logic detector (2×2×10 mm$^3$ LYSO crystals) and inter-crystal positioning algorithm. Discrimination of smaller cross-section crystals for improved spatial resolution can be achieved by using smaller size PMTs and designing an appropriate lightguide. The instant simulation results (FIG. 16) allow confidence that this goal may readily be achieved by the instant detector designs. However, using longer crystals for improve sensitivity will increase parallax effect in the scanner resulting in some spatial resolution degradation as a function of radial position. This effect requires careful simulation studies for an optimal detector design, as described infra.

Preliminary results also indicate that for a 2×2×10 mm$^3$ LYSO crystal with a polished surface finish a coincidence timing resolution of 300 ps can be achieved if special care is paid to the choice of PMT and timing electronics. However, when using smaller and longer crystals for higher resolution and sensitivity, this number may degrade partly due to the effects of DOI on the signal. Measurements will assist in the determination of the full impact of crystal size, surface finish, and DOI on the timing resolution. This will be followed by system simulations performed to determine an appropriate combination for use in a high performance scanner (Example 4, below). In addition, electronics processing techniques will be developed to maintain the good timing resolution in long crystals.

Example 4

Figure 18:
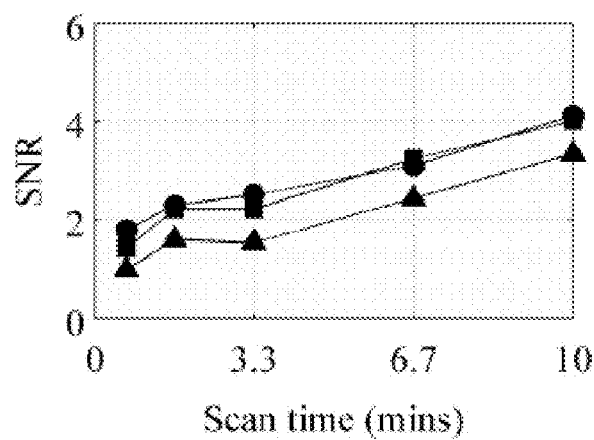
FIG. 18 provides SNR values for Lesion 1 (5-mm diameter) in a 10-cm diameter phantom placed in Full ring Non-TOF scanner (●), a two-third ring 300 ps TOF scanner (■), and a two-third ring 600 ps TOF scanner (▲). The spatial resolution was 1-mm for all designs.

Demonstration of Whether TOF Information can Compensate for Missing Projection Data in Proposed Scanner Geometry Simulated images were used for data shown in FIG. 8, and calculation was made of a simple measure of signal-to-noise (SNR) given by:

$$SNR = \frac{\frac{C_H}{C_B} - 1}{\sqrt{\left(\frac{\sigma_H}{C_H}\right)^2 + \left(\frac{\sigma_B}{C_B}\right)^2}}$$

where $C_H$ and $\sigma_H$ are the mean and standard deviation of counts in an ROI drawn over the lesion, and $C_B$ and $\sigma_B$ are the mean and standard deviation of counts in a background ROI. For the background, ROIs were drawn as annular regions beyond the sphere diameter in order to reduce effects arising due to the non-uniformities and artifacts in some of the reconstructed images that will lead to an incorrect estimation of the background counts. This SNR metric, though not representative of absolute lesion detection, represents a simple way to assess scanner performance and is proportional to lesion detection in a signal known exactly task. In clinical whole-body imaging it has been shown that TOF imaging leads to increases in image SNR values especially as the imaging object increases in size. In breast imaging, increase in SNR, if any, is expected to be small. FIG. 18 shows the SNR values calculated for Lesion 1 in three scanner designs as a function of scan time. The scan times were calculated by assuming a 15-mCi $^{18}$F-FDG injection followed by a 1 hour uptake period and a detector using 15-mm long LYSO crystals. Note that scan times vary up to 10 minutes since the lesion size and uptake being investigated here represent challenging breast imaging situations of early stage cancer that cannot be detected or quantified in a clinical PET scanner. The spatial resolution was 1-mm for the simulated scanners. With a timing resolution of 300 ps, the two-third ring TOF scanner performs at least as well as a conventional Full ring Non-TOF scanner. However, with a 600 ps timing resolution and slightly longer scan times, it is possible to achieve SNR values in a two-third ring scanner that are similar to the Full ring Non-TOF scanner. These results are consistent with what was qualitatively observed and shown earlier in FIGS. 5 and 9.

By using TOF information, many of the distortions as well as non-uniform artifacts can be reduced without the need for detector rotation. However, as the angular coverage is reduced, better timing resolution is needed to produce artifact-free images. In particular, a timing resolution of 600 ps or better is needed for a two-third ring scanner (scanner ring diameter of 15-cm) in order to achieve hot lesion CRC values similar to a full ring scanner (see FIG. 10). This suggests that there will eventually be a trade-off in the design of such PET scanners where the timing resolution will be determined by detector performance which, in turn, will define the minimum angular coverage needed in the scanner for artifact or distortion-free images without detector rotation. Another possibility includes splitting the two detectors into four smaller non-contiguous detectors (see, e.g., FIG. 2D) to expand the range of angular coverage in the scanner, which will also affect the scanner cost in terms of number of crystals and PMTs.

Since limited angle tomography also leads to a reduction in sensitivity relative to a Full ring scanner due to the loss of counts in the missing LORs, the relative sensitivity of various scanner geometries was calculated relative to a Full ring Non-TOF scanner. Table 5, below, shows this sensitivity value, which is simply a product of the relative geometric sensitivity (due to missing LORs) and the simple TOF gain given by Budinger (71) as $D/\Delta x$, where D is the object diameter (10-cm for these calculations) and $\Delta x = c \cdot \Delta t/2$ (where c is the speed of light and $\Delta t$ is the fwhm of the scanner timing resolution).

TABLE 5

|  | Timing resolution (ps) | $D/\Delta x$ | Relative geometric sensitivity | Relative absolute sensitivity |
|---|---|---|---|---|
| Full ring | 300 | 2.2 | 1.0 | 2.2 |
|  | 600 | 1.1 | 1.0 | 1.1 |
| Two-third ring | 300 | 2.2 | 0.44 | 1.0 |
|  | 600 | 1.1 | 0.44 | 0.5 |

The expected changes in absolute sensitivity as derived from these first principles are in reasonable agreement from the results for the hot lesion SNR values. In particular the two-third ring scanner with 300 ps timing resolution has similar performance to the Full ring Non-TOF scanner.

Experimental Methods.

As shown by the preceding results, the performance of a complete scanner will be a function of its spatial resolution, timing resolution, geometry, and sensitivity. One objective is to demonstrate through Monte Carlo simulations the extent to which TOF information helps compensate for the missing projection data in a partial ring geometry. In particular the trade-off between angular coverage and timing resolution may be investigated. Next, simulations are performed for varying sets of parameters for the scanner geometry (ring diameter, axial length, and percent of complete ring), spatial resolution (with and without DOI measurement), and timing resolution, as well as sensitivity to understand the impact on resultant images and clinical diagnosis. In particular, increasing crystal length will translate into improved sensitivity, but also lead to a potential degradation in energy and timing resolutions due to a loss of scintillation light in the crystal, and degradation in spatial resolution if DOI information is not available. The scanner ring geometry will be varied based upon the crystal timing resolution in order to achieve artifact-free images. Phantoms similar to that shown in FIG. 4 will be simulated. As shown previously in FIG. 8, it is very clear that improved spatial resolution leads to better CRC for small hot lesions, while improved timing resolution is needed as the polar angle coverage in the scanner is reduced. The impact of crystal length and loss of sensitivity due to a partial ring will also have an effect on the collected statistics and noise in the image leading to potentially long scan times. The increased scan time (or reduced sensitivity) for partial ring scanners becomes more relevant when one takes into account the primary use of the dedicated breast scanner, used either as an immediate follow-up imaging modality to a clinical whole-body scan, or used in a dynamic imaging mode for a tumor quantification task. Hence, these results indicate, that the eventual scanner design will need to optimize the crystal length (for increased sensitivity), crystal cross-section, and timing resolution to achieve the good performance in partial ring geometry in practical scan times. Specific parameters for spatial, energy and timing resolutions based upon the results obtained in Example 3 for 10-20 mm long and 1.5×1.5-2×2 mm² cross-section LYSO crystals will also be evaluated. One important consideration in these simulations will be to determine a practical, non-DOI measuring detector design from Example 3, above, that provides relatively high performance. Separate metrics for lesion detection and uptake estimation, as well as point source spatial resolution, will be used.

Lesion Detection Metric.

Oncologic breast imaging generally involves detection of cancerous lesions followed by an estimation of amount of activity uptake in these lesions. For estimation tasks the CRC metric is used as a measure of lesion uptake estimation in the scanner. For lesion detection tasks numerical observers are used to better characterize and optimize the performance of this scanner design. Current research on model observers (72-77) has concentrated on linear observers computing the model response $\lambda$ as a scalar product $\lambda = w \cdot f$ between a template of weights, w, and the image, f. There are several model observer approaches considered in the literature, including the region-of-interest (ROI) (78), non-prewhitening matched filter (NPWMF) (79), non-prewhitening with eye filter (NPWE) (80), Hotelling observer (81), channelized Hotelling observer (CHO) (82-86), and channelized non-prewhitening (CNPW) observer (87, 88). An ideal observer using matched filters has been advocated to measure instrument performance (89), whereas CHO and the CNPW observer have been found to provide the closest match to human observers (88, 90). The NPWMF and CHO may be used for a signal-known-exactly/backgroundknown-exactly lesion detection task for optimizing the scanner design.

Figure 19:
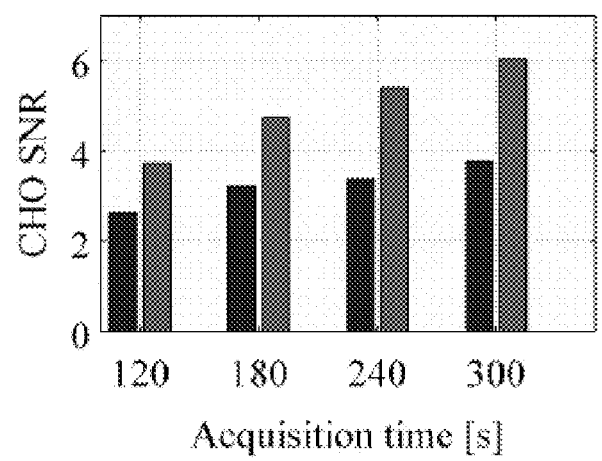
FIG. 19 provides a chart showing the CHO SNR values as a function of scan time for TOF (light bars) and Non-TOF (dark bars) reconstructions. There is a systematic improvement with TOF reconstruction for all scan times. Data were acquired on clinical Philips Gemini TF PET/CT scanner.

These lesion detectability measures have been used in characterizing the improved TOF performance of a new generation of whole-body TOF PET scanners. FIG. 19 provides a plot for lesion detectability as measured with the CHO SNR value for varying scan times and TOF and Non-TOF reconstructions in the Philips Gemini TF scanner. The data were collected for 10-mm diameter lesions placed in a large 35-cm diameter cylinder with an uptake ratio of 6:1 with respect to background (60). In this plot improved lesion detectability is observed for TOF images, with the CHO SNR value for a 120 s scan time with TOF being similar to the CHO SNR value for a 300 s scan time without TOF information. Similar lesion detectability measures are used to optimize the breast scanner design.

Lesion Uptake Estimation.

For lesion uptake estimation task the contrast recovery coefficient (CRC) is used as prescribed in the NEMA NU2-2001 standards. The CRC value is determined for small, hot lesions over multiple realizations of the image to arrive at an ensemble average. High CRC values in small lesions are necessary for quantitative PET data, and the subsequent staging of cancer in the patient.

Spatial Resolution and Impact of DOI.

Simulations will be performed for point source spatial resolution as a function of radial position in the scanner. The goal will be to benchmark the impact of parallax error as a function of crystal size and the relative benefit of a DOI measurement.

Example 5

Developing a Coincidence Detector Setup in an Imaging Gantry and Performing Basic Phantom Measurements Mechanical and Gantry Setup.

Figure 20:
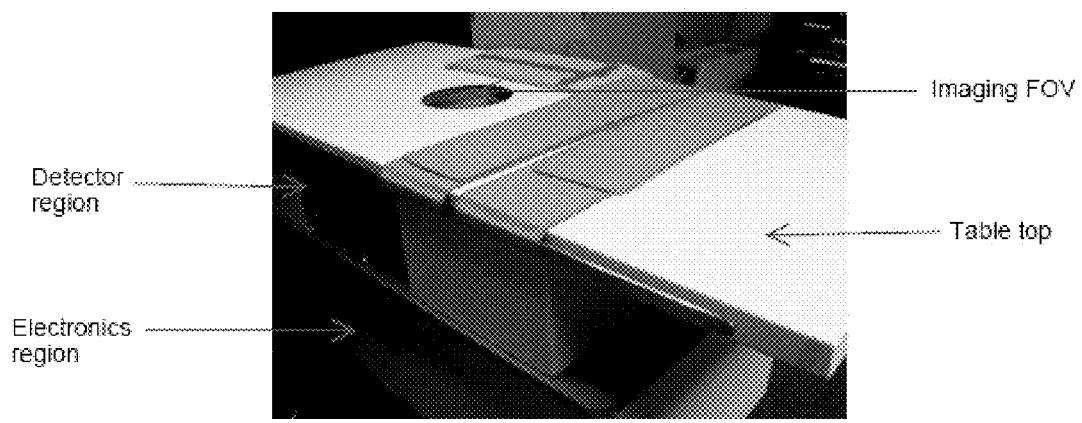
FIG. 20 shows a scanner gantry that may be used for imaging with the inventive BPET breast scanner.

Two coincident detector arrays (15×15 cm² each) were developed based upon the detector designs evaluated in Examples 3 and 4. While the simulations used curvilinear detector geometry, the prototype design can use rectilinear (flat) detectors for ease of construction. The detectors are retro-fitted into an existing gantry that was developed for use in an existing NaI(Tl)-based breast scanner (BPET) (40). As shown in FIG. 20, it is similar to a prone mammography table with a thin patient table to minimize dead space between the chest wall and the detectors. The patient lies prone on top of the thin patient table with the breast lying between the detectors through the opening on top. The detectors lie directly below the table, with the electronic stored in the lowest level of the gantry. The detectors lie on adjustable rails allowing for a variable detector separation. Below the detector region, the gantry has additional space where the electronics are kept. For some measurements, additional data may be acquired by rotating the detectors in order to provide larger angular coverage of the FOV and study the impact on resultant images. Since this is a proto-type scanner developed to evaluate the performance of our design, the gantry will not accommodate axilla measurements or front/back chest for small breasts (as shown in FIG. 1A).

This work is intended to demonstrate the feasibility of a high performance partial ring TOF scanner in achieving quantitative images without detector rotation. A successful partial ring design in this work will then provide the flexibility to design an appropriate mechanical setup for the axilla and chest wall imaging in the future.

Figure 21:
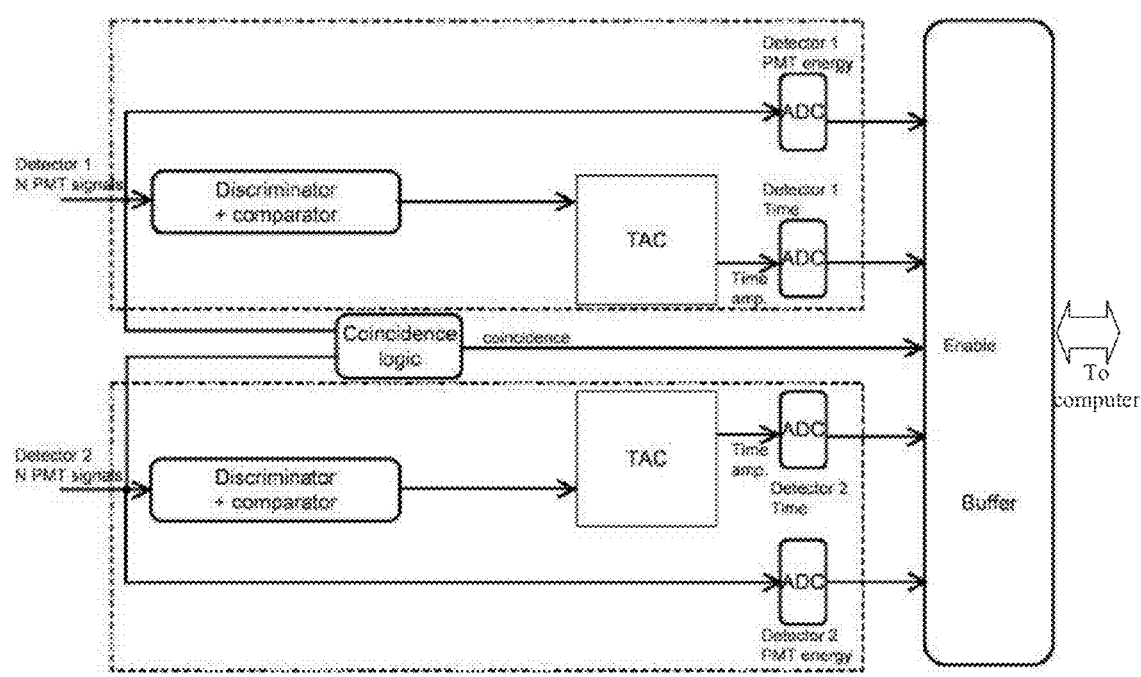
FIG. 21 depicts a schematic for the general electronics architecture for performing basic imaging measurements with subsections of two coincident detectors. The dotted regions represent the circuitry which will be a part of the electronics that is currently being developed for a whole-body $LaBr_3$ TOF PET scanner.

The general electronics architecture may be based upon work performed recently in developing a prototype LaBr$_3$-based whole body PET scanner. A modified version of the schematic for the implementation is shown in FIG. 21. The PMT signals from each detector pass through a leading edge discriminator board to generate precise timing information for the events. A window comparator is used to restrict signals to those events that deposit energies close to 511-keV. Such a circuit design that performs the timing pickoff for the LaBr$_3$ TOF PET scanner has already been designed and implemented. The intrinsic jitter for this circuit when measured with a pulser is 46 ps. Detector measurements in the laboratory with these electronics show a timing resolution of about 300 ps, while the complete system timing resolution on the LaBr$_3$ TOF PET scanner is 400 ps. The signal processing part of this electronics also has the flexibility of measuring charge and timing at several signal amplitudes along the signal rise time, a capability which is important in reducing the impact of DOI on measurement of the signal arrival time (see earlier discussion in Example 3). This circuit design will need only minor modifications to accommodate the number of PMT channels used for coincidence measurements.

As shown in FIG. 21, the timing signals are then passed through a TAC to convert the time signals into voltage levels followed by free-running ADCs for digitization of the time. The TAC that is presently proposed for use is similar to what was developed for the LaBr$_3$ TOF PET scanner, which in turn was based on a design developed for the CDF (Collider Detector Facility at Fermilab) (67) TOF system by the HEP engineering group at the University of Pennsylvania. Simultaneously, separate banks of free-running ADCs will also digitize the individual PMT signals for charge or energy readout. All data will be stored in a buffer that is enabled by a coincidence signal formed using a coarse timing circuitry. Most of the basic principles and design of the individual electronics component have been successfully developed and tested for the LaBr$_3$ TOF PET scanner, and minor modifications will be needed to adapt to the number of channels needed for the coincident breast system.

Energy and Timing Calibrations.

The energy and timing calibrations will be based upon some modifications to our current techniques as implemented on the LaBr$_3$ TOF PET scanner. Gross effects due to differences in individual PMT channel gain values and transit times will be corrected by an appropriate design of the PMT base, a technique employed successfully with respect to the LaBr$_3$ scanner. The additional energy and timing calibrations are intended to perform corrections for differences in intrinsic properties of individual crystals, as well as effects arising due to the crystal position within the detector. For energy calibrations, correction tables will be generated by using a 22Na point source and calculating the peak position in the energy spectrum for each crystal and normalizing it to a common value. For timing calibrations a 22Na point source in a brass block will be placed at the center of the scanner. The difference in arrival times for all coincident photons are recorded and timing histograms generated for all possible lines-of-response (LORs). The source position and hence the correct difference in arrival times is also known (zero for a centered source). A timing correction factor is then generated for each LOR as the difference in the centroid of its measured timing histogram versus the correct difference in arrival time. These techniques have been implemented on our LaBr3 scanner and perform well. A detector map of the measured timing offsets with this technique on the LaBr3 scanner was generated, a color scale being used to indicated that the timing offsets vary by +/−1 ns over the entire scanner (not shown). After correcting for these timing offsets, a fairly uniform timing resolution of about 400 ps was observed over the entire scanner, indicating the efficacy of the timing calibration technique.

Measurements, Data Corrections, and Image Reconstruction.

As a final step in the design evaluation measurements are performed for basic physical properties as well as simple imaging tasks using the coincident pair of detectors. By rotating the phantom it is possible to cover the full angular FOV in the transverse plane. The first set of data collection involves measurements for the intrinsic energy and timing resolution achieved in the two detectors. This is followed by measurements with small point sources placed at different radial positions within the FOV. The point source data collected at all rotation angles is then reconstructed using a Fourier space filtered back-projection algorithm (3DFRP) (91) to characterize the reconstructed spatial resolution in the scanner. In particular, the benefit of inter-crystal positioning on the final reconstructed spatial resolution is evaluated, as well as parallax effects for off-center source positions.

Finally, simple lesion phantoms similar to the one simulated (see FIG. 4) may be constructed to perform imaging measurements. Data is acquired for several rotation angles, and sub-sections of the data are reconstructed to experimentally characterize the quality of tomographic images that can be acquired with the breast scanner design as a function of polar angle coverage. For attenuation and scatter correction, the ideas developed for the BPET scanner which resulted in successful quantitative images in phantoms and patients will be expanded (see FIG. 12). For attenuation correction, an analytical model using cylinders of different sizes may be evaluated. Since the breast represents a fairly homogeneous tissue density this technique has worked well in the BPET scanner studies. For scatter correction it is possible to reduce as many events as possible through shielding and energy gating.

Figure 11:
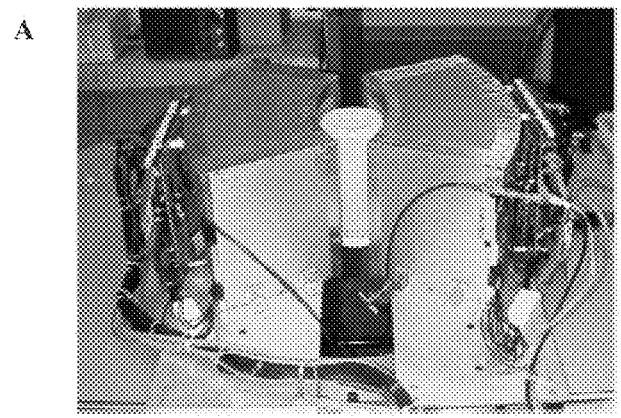
FIG. 11A shows a picture of two continuous, curve plate NaI(Tl) detectors used in BPET scanner.
FIG. 11B provides a schematic view of a woman lying prone on the BPET scanner table with the breast lying between the two detectors. As shown, there is a ¼" lead shielding just below the tabletop to shield the detectors from out-of-field activity.
Figure 11:
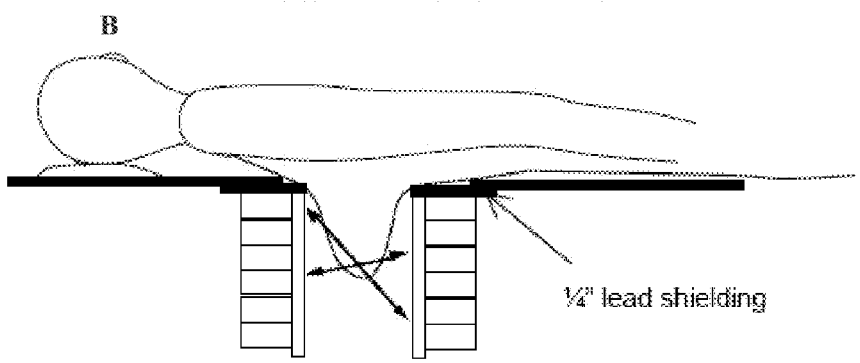

As shown in FIG. 11, the existing BPET scanner gantry that may be used for this breast scanner project has a ¼" lead shielding below the thin patient table to reduce events (including scatter) from out-of-field activity. This thickness is adequate for shielding from out of field activity since most of those photons make oblique angles with the shielding plane and so their paths in the lead are longer than the ¼" thickness. In addition, the energy threshold of the scanner will be raised high in order to reject events which lie outside the photo-peak. Finally, a model based, TOF-extended, single scatter simulation (92) will be adapted, originally developed for the prototype LaBr3 scanner (45, 63), for use with the new breast scanner and subtract any scattered coincidences in the measured data.

Image reconstruction is performed with a modified version of a list-mode version of the ML-EM algorithm (93) using smooth, localized basis functions ('blobs') on a body-centered cubic grid (94) with a TOF kernel applied in both the forward- and back-projection operations. Attenuation and detector efficiency are included in the iterative reconstruction as multiplicative factors; scatter and randoms (estimated from the delayed events) are added to the result of the basic forward-projection operation. The TOF response function is modeled as a one-dimensional Gaussian function along the LOR. The ML-EM algorithm is accelerated by dividing the data into chronologically ordered subsets (93). This algorithm was originally developed for use with a proto-type LaBr$_3$ TOF PET scanner (45) and a modified version has been commercially implemented on the Philips Gemini TF PET/CT (46). The primary modification for its use in a limited angle breast scanner geometry will be an appropriate masking in the sensitivity image of those polar angles which are absent in a partial ring scanner design. Most of these ideas have been implemented successfully in reconstruction of the simulation images as shown supra. Quantitative measurements for lesion uptake (CRC) as well as lesion detectability are performed to benchmark the experimental performance of this design with the simulated results from Example 4.

Example 6

Additional Breast Scanner Simulations

Simulations were performed for a breast scanner design with a ring diameter and axial length of 15-cm and including a Full (180 degree in-plane angular coverage), ⅔ (120 degree in-plane angular coverage), or ½ (90 degree in-plane angular coverage) ring detector. Results (below) show that as the angular coverage decreases, improved timing resolution is needed to achieve distortion and artifact-free images. The CRC value for small hot lesions is similar in these situations to a Full ring Non-TOF scanner. Results indicate that for this geometry a timing resolution of 600 ps or better is needed for a ⅔ ring scanner, while a timing resolution of 300 ps or better is needed for a ½ ring scanner. The hot lesion SNR values are similar to the expected sensitivity improvement arising from TOF reconstruction and the loss in sensitivity due to reduced geometric sensitivity in a limited angle coverage PET scanner. In particular, it is possible to maintain similar SNR characteristic in a ⅔ ring scanner with a timing resolution of 300 ps as in a Full ring Non-TOF scanner.

Monte Carlo simulations were performed for a breast scanner design in order to understand the benefit of TOF in reconstruction of limited angle PET data. The Monte Carlo simulation is based on an EGS4 simulations package which models annihilation photon emission and transmission (with attenuation and scatter) through a geometric phantom, tracks their subsequent passage through a scintillation detector configuration, models the detector light response and point spread function as well as timing resolution, and outputs a listmode data set where each event is tagged as scattered (in the phantom) or true (unscattered) event (see L. E. Adam and C. C. Watson, "*Experimental determination of the lower energy discriminator level of a positron emission tomograph*," Nuklearmedizin-Nuclear Medicine, vol. 38, pp. 61-65, 1999; S. Surti, J. S. Karp, and G. Muehllehner, "*Image quality assessment of LaBr$_3$-based whole-body 3D PET scanners: a Monte Carlo evaluation*," Phys. Med. Biol., vol. 49, pp. 4593-4610, Oct. 7, 2004; S. Surti, J. S. Karp, L. A. Popescu, M. E. Daube-Witherspoon, and M. Werner, "*Investigation of time-of-flight benefit for fully 3-D PET*," IEEE Trans. Med. Imag., vol. 25, pp. 529-538, May 2006). In this work only the true coincidences were reconstructed. The simulated scanner had a ring diameter of 15-cm and axial length of about 15-cm. Three different LSO crystal sizes were simulated for the detector: $1 \times 1 \times 10$-mm$^3$, $2 \times 2 \times 10$-mm$^3$, and $3 \times 3 \times 10$-mm$^3$.

The simulated phantoms were a 10-cm diameter by 8-cm long and a 6-cm diameter by 8-cm long cylinder, each containing three 5-mm diameter hot spheres with 8:1 uptake with respect to background, and one cold sphere. The scan times were calculated by assuming a 15-mCi $^{18}$F-FDG injection followed by a 1 hour uptake period leading to an $^{18}$F-FDG concentration of 0.0975-µCi/cc in the breast (representative of the average radiotracer concentration in normal breast tissue—see K. R. Zasadny and R. L. Wahl, "*Standardized uptake values of normal tissues in PET with 2-[Fluorine-18]-fluoro-2-deoxy-D-glucose: variations with body weight and a method for correction*," Radiol., vol. 189, pp. 847-850, 1993).

Image reconstruction was performed using data from a full scanner ring (complete 180 degree in-plane angular coverage), a two-third scanner ring (120 degree in-plane angular coverage), and a half scanner ring (90 degree in-plane angular coverage) (see FIG. 4). For image reconstruction a 3D listmode iterative reconstruction algorithm was used, employing chronologically ordered sub-sets. This algorithm uses a Gaussian TOF kernel for TOF reconstructions. Using 33 sub-sets, it was found that 3-6 iterations of the reconstruction algorithm may be used, depending upon the timing resolution, to achieve maximum contrast for the hot lesions.

For quantitative analysis a contrast recovery coefficient (CRC) metric was used to estimate the sphere uptake accuracy for the hot spheres. For this calculation, regions-of-interest (ROIs) were drawn over the hot and cold spheres, equal in size to the sphere diameters, to obtain the mean counts ($C_H$ for the hot, and CC for the cold lesion) Annular regions beyond the sphere diameter were drawn to estimate the background counts ($C_B$). The background ROIs were drawn locally in this manner due to the non-uniformities and artifacts which arise in some of the reconstructed images that will lead to incorrect estimation of the background counts. CRC for hot spheres was calculated using the NEMA definition (see Example 1, above). In addition, a simple measure of signal-to-noise (SNR) was also calculated using the formula described in Example 4, above.

Results. Impact of Crystal Size.

Figure 22:
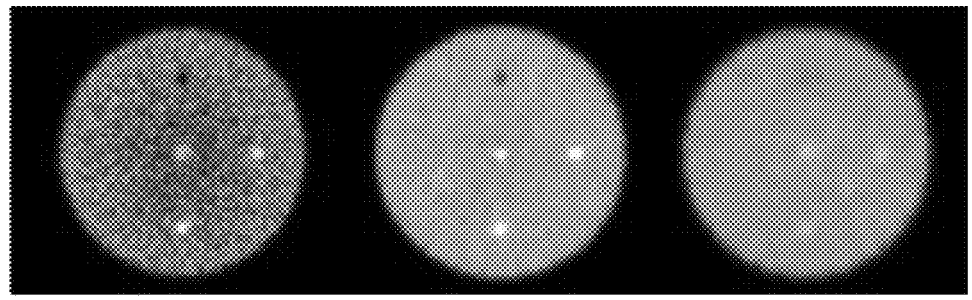
FIG. 22A provides reconstructed images for a central transverse slice from a Full ring scanner using three different crystal cross-sections.
FIG. 22B depicts measured CRC values for the three hot lesions in a Full ring scanner using three different crystal cross-sections; the bars labeled "1×1", "2×2", and "3×3" correspond to scanners using 1×1 mm², 2×2 mm², and 3×3 mm² crystals, respectively.
Figure 22:
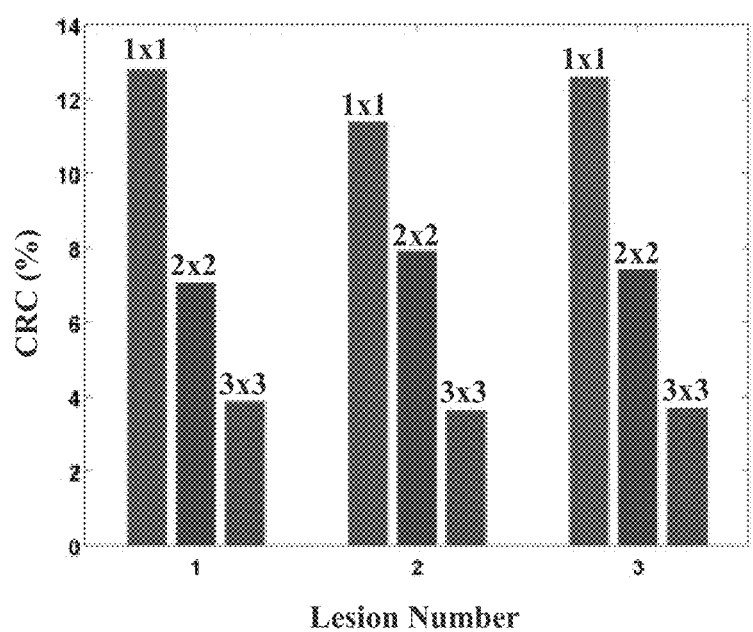

FIG. 22A shows the reconstructed images for a Full ring scanner for the three crystal cross-sections investigated. Visually, it is very clear that the contrast in the three hot lesions decreases as the crystal size is increased. This is quantitatively observed in FIG. 22B, which shows the CRC value for the three hot lesions decreasing noticeably as the crystal cross-section is increased to $3 \times 3$ mm$^2$. A similar trend was observed for the cold lesion (Lesion 4) where the CRC values were 46%, 35%, and 16% for crystal cross-sections of to $1 \times 1$ mm$^2$, $2 \times 2$ mm$^2$, and $3 \times 3$ mm$^2$, respectively. All subsequent evaluations were performed for a scanner using $1 \times 1 \times 10$ mm$^3$ crystals.

Impact of TOF on Limited Angle Reconstruction of Data from a Small Object.

Figure 23:
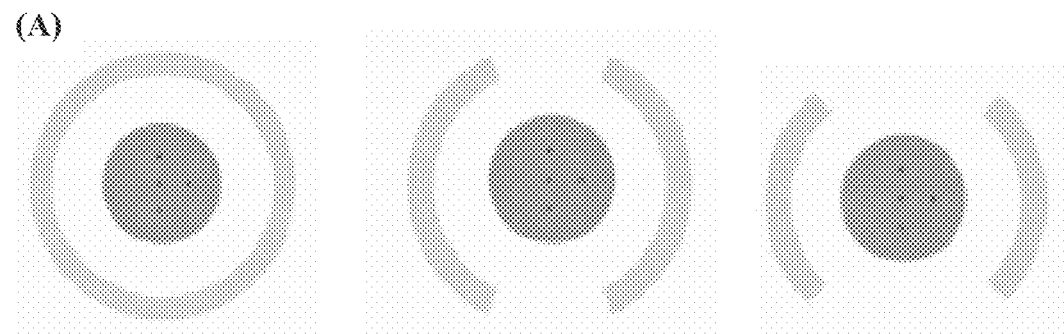
FIG. 23A provides a schematic of detector arrangement for a Full ring (Left), ⅔ ring (Middle), and ½ ring (Right) scanner.
FIG. 23B provides reconstructed images for a central transverse slice of a 6-cm diameter cylindrical phantom. The top row shows TOF reconstructed images (timing resolution of 200 ps), while the bottom row has the Non-TOF images. The crystal size for these simulations was 1×1×10 mm³.
Figure 23:
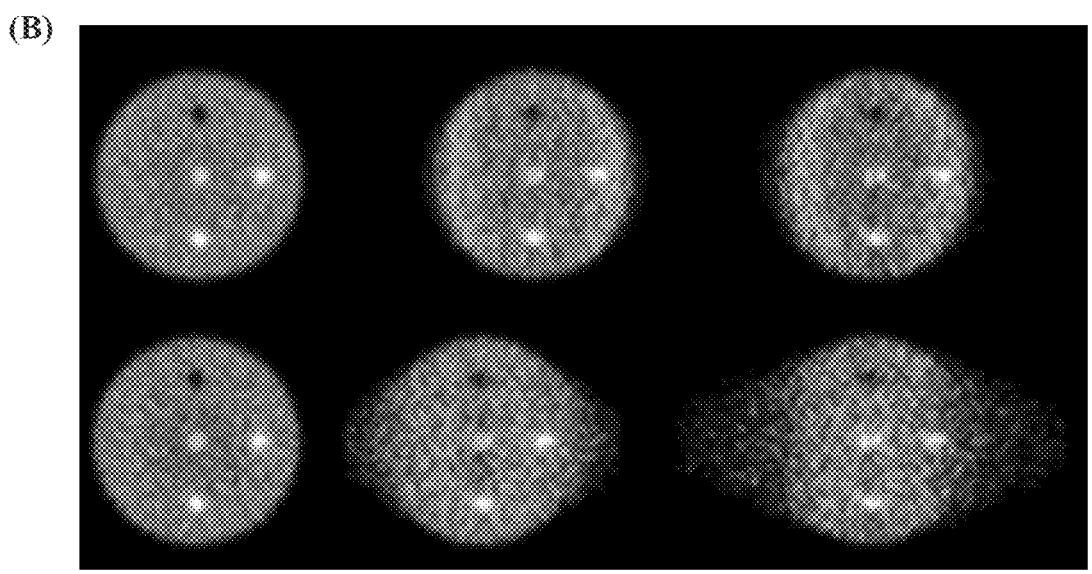

FIG. 23 shows the central transverse slice for reconstructed images for the 6-cm diameter phantom. As the angular coverage is reduced (moving from Full ring through ⅔ ring to a ½ ring scanner) there is increased distortion in the image in a direction perpendicular to the detectors. With TOF information (timing resolution of 200 ps), this distortion is greatly reduced.

Impact of TOF on Limited Angle Reconstruction of Data from a Large Object.

Figure 24:
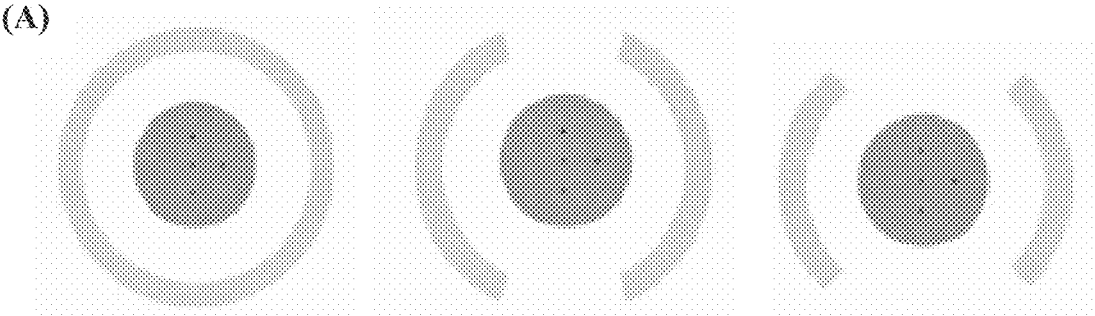
FIG. 24A provides a schematic of detector arrangement for a Full ring (Left), ⅔ ring (Middle), and ½ ring (Right) scanner.
FIG. 24B provides reconstructed images for a central transverse slice of a 10-cm diameter cylindrical phantom. The top row shows TOF reconstructed images (timing resolution of 200 ps), while the bottom row has the Non-TOF images. The crystal size for these simulations was 1×1×10 mm$^3$.
Figure 24:
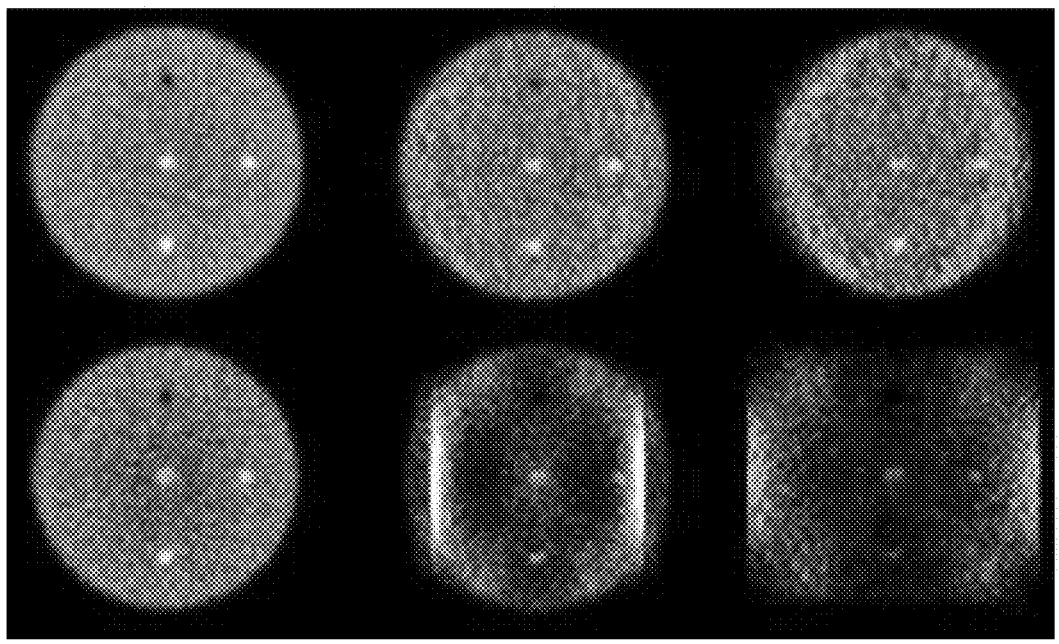

FIG. 24 shows the central transverse slice for reconstructed images for a larger 10-cm diameter phantom. Now, as the angular coverage is reduced (moving from Full ring through ⅔ ring to a ½ ring scanner) there are significant artifacts in the Non-TOF reconstructed images due to missing angular views. The TOF information still leads to more realistic reconstructed images with reduced artifacts. The two bright vertical strips in the ⅔ ring scanner Non-TOF reconstruction are due to the acceptance of LORs within the same detector at its two edges, an effect that in practice will not be present since LORs with both end-points in the same detector are rejected.

Impact of TOF on CRC Achieved in Limited Angle Tomography.

Figure 25:
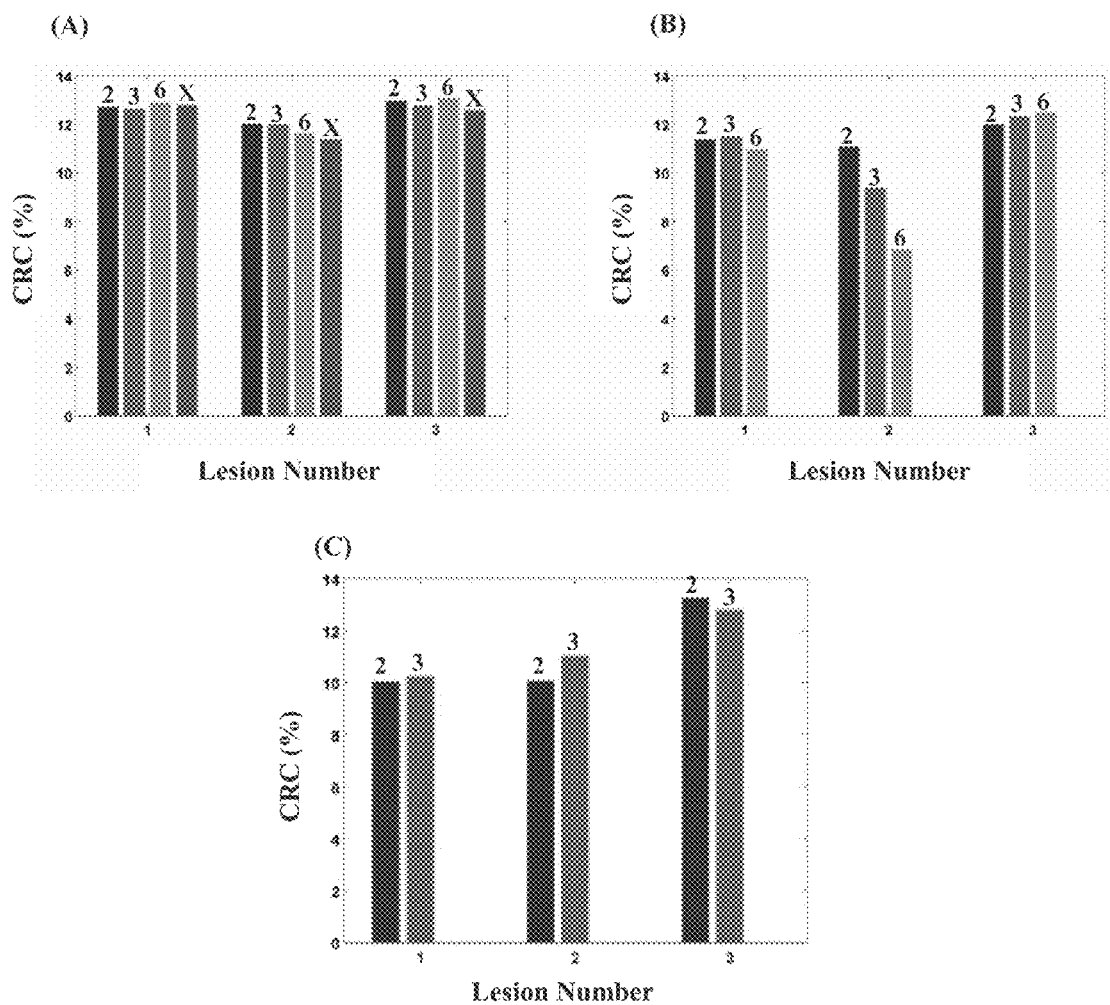
FIG. 25 shows CRC values for Lesions 1, 2, and 3 in a 10-cm diameter phantom for a Full ring (A), ⅔ ring (B), and ½ ring (C) scanner. The bars marked "2", "3", "6", and "X" are for 200 ps TOF, 300 ps TOF, 600 ps TOF, and Non-TOF scanners, respectively. Results are only shown for those images that were deemed relatively artifact-free. The crystal size for these simulations was 1×1×10 mm$^3$.
Figure 26:
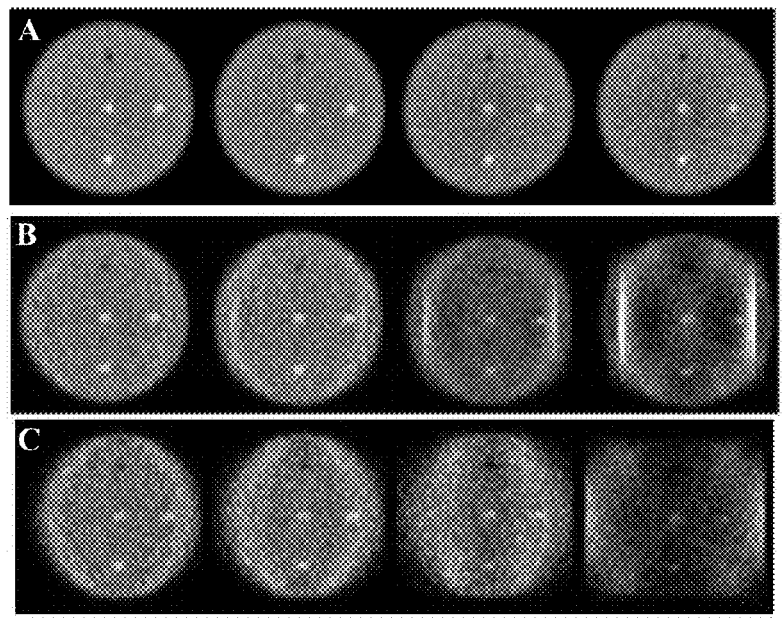
FIG. 26 shows the central transverse slice from reconstructed images for a 10-cm diameter cylindrical phantom in (A) Full ring, (B) ⅔ ring, and (C) ½ ring scanners. With each set, the four images moving left to right are: 200 ps TOF, 300 ps TOF, 600 ps TOF, and Non-TOF. The crystal size for these simulations was 1×1×10 mm$^3$.

FIG. 25A shows the measured CRC values for the three hot lesions (Lesion 1, 2, and 3) in the Full, ⅔, and ½ ring scanners as function of timing resolution. The results are shown only for those images that were deemed to be relatively artifact-free for analysis. The results show that TOF imaging has no impact on the CRC values achieved in the Full ring scanner. For the ⅔ ring scanner, a timing resolution of 600 ps or better leads to CRC values which are similar to those achieved in the Full ring scanner. The drop in CRC seen for lesion 2 in the ⅔ ring scanner with 600 ps TOF reconstruction is due to bright vertical strips seen in the image due to LORs with end-points near the edges of the same detector. As a result the background estimate for this lesion is higher leading to a reduction in the CRC for that lesion. For the ½ ring scanner, on the other hand, our results indicate that a timing resolution of 300 ps or better still helps achieve CRC values for all three lesions which are similar to those achieved in the Full ring scanner. For a qualitative comparison, FIG. 26 also shows the central slices for the reconstructed images for the three scanner geometries as function of timing resolution. It is obvious that for the ½ ring scanner (FIG. 26C), 600 ps TOF and Non-TOF images have significant artifacts, while for the ⅔ ring scanner (FIG. 26B) the Non-TOF image has the most significant artifacts. The results for the Full ring scanner are shown in FIG. 26A.

Impact of TOF on SNR Achieved in a Full Ring Scanner.

Figure 27:
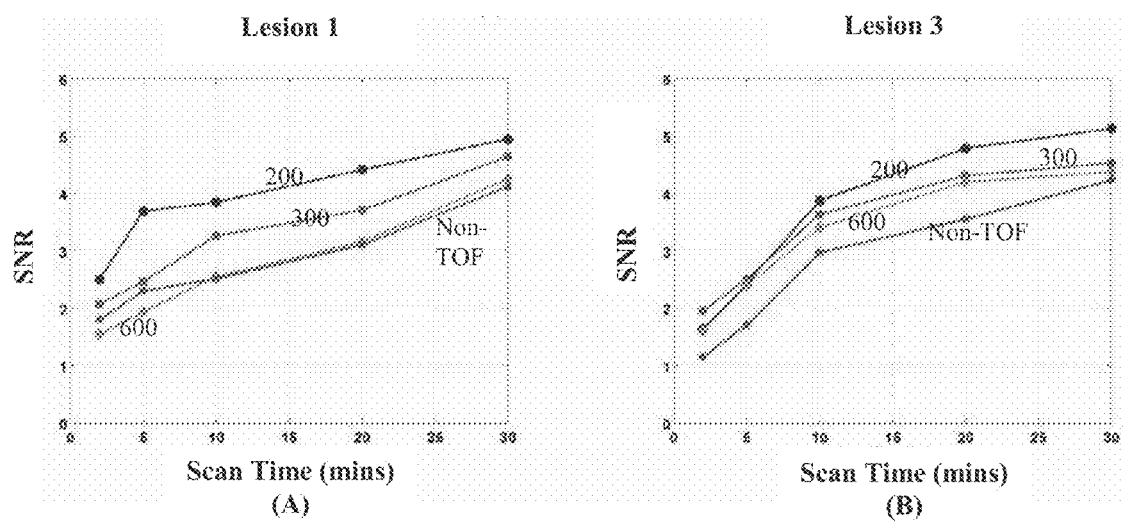
FIG. 27 depicts SNR values for (A) Lesion 1 and (B) Lesion 3 in a 10 cm diameter phantom placed in a Full ring scanner with varying timing resolution. Curves are labeled for 200 ps TOF, 300 ps TOF, 600 ps TOF, and Non-TOF scanners. The crystal size for these simulations was 1×1×10 mm$^3$.

In clinical whole-body imaging it has been shown that TOF imaging leads to increases in image SNR values, especially as the imaging object increases in size. In breast imaging the increase in SNR, if any, is expected to be small. FIG. 27 shows the SNR values calculated for Lesion 1 and 3 in a Full ring scanner as a function of scan time; these results indicate that there is some gain in the SNR achieved for the two lesions with very good timing resolution of 200-300 ps. If such high timing resolution can be achieved in a PET detector, then one can expect a basic SNR improvement with TOF information even in a Full ring PET scanner.

Impact of Timing Resolution on SNR Achieved in Limited-Angle TOF Scanners.

Since limited angle tomography will also lead to a reduction in scanner sensitivity, the impact on SNR for limited angle scanners with TOF information was investigated. Again, the analysis was restricted to those situations that produced relatively artifact-free images.

Figure 28:
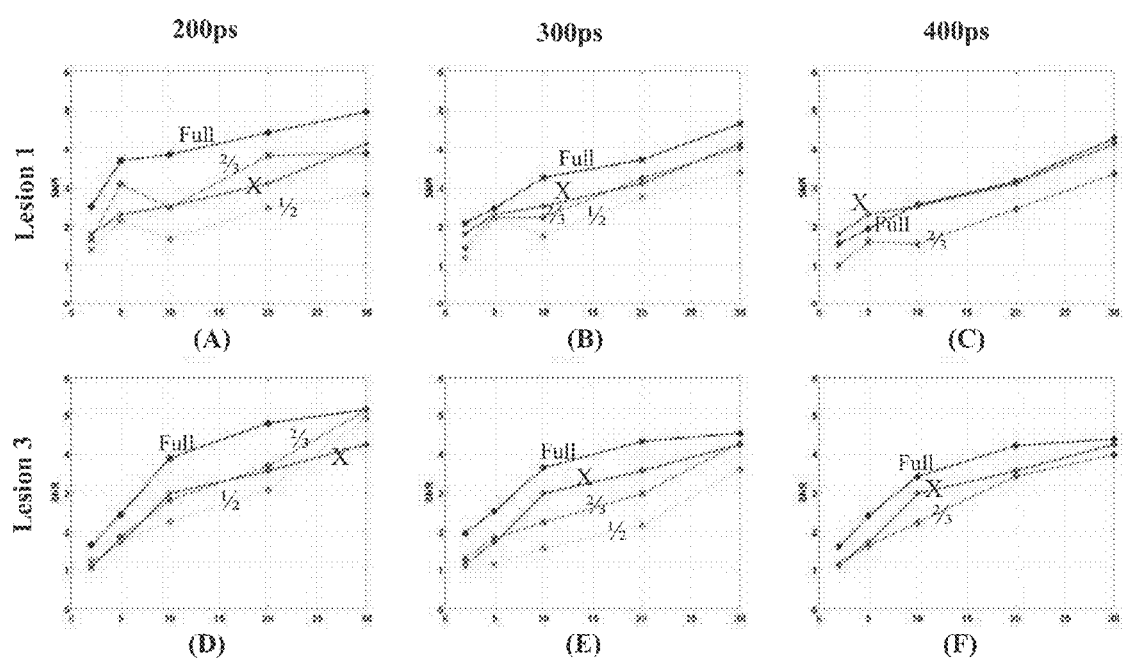
FIG. 28 depicts SNR values vs. scan time for lesions 1 (A, B, and C) and 2 (D, E, F) for a 200 ps (A and D), 300 ps (B and E), and 600 ps (C and F) timing resolution TOF scanner. Curves for the Full, ⅔, and ½ ring TOF scanners are marked accordingly. For comparison, the results from a Full ring Non-TOF scanner are also shown and marked "X". All results are for the 10-cm diameter cylindrical phantom. Results are only shown for those images that were deemed relatively artifact-free. The crystal size for these simulations was 1×1×10 mm$^3$.

FIG. 28 summarizes the results. With a timing resolution of 300 ps and better, the ⅔ ring TOF scanner performs at least as well as a conventional Full ring Non-TOF scanner while the ½ ring scanner requires longer scan times to achieve similar performance. With a 600 ps timing resolution, a Full ring TOF scanner has no noticeable advantage over a Full ring Non-TOF scanner. However, with this timing resolution and slightly longer scan times, SNR values can be achieved with a ⅔ ring scanner that are similar to the Full ring Non-TOF scanner.

The present Example demonstrates the benefit of using TOF information for generating distortion or artifact-free images in a limited angle, emission tomography situation such as that encountered in dedicated breast PET imaging. In particular, without TOF information, the limited angle situation leads to not only distortions, but also severe artifacts in the reconstructed image as the object size relative to the scanner ring diameter increases. The reconstructed image in this situation for a warm cylinder with hot/cold lesions has large non-uniformities in the background. This greatly limits the use of such a PET scanner in quantitative imaging situations, especially those where the scanner ring diameter is small in order to achieve high geometric sensitivity. Consequently, under such circumstances, detector rotation must be employed to cover all the missing LORs, which however leads to longer scan times or essentially a reduction in effective sensitivity.

In contrast, by using TOF information, much of the distortion as well as non-uniform artifacts can be reduced without the need for detector rotation. However, as the angular coverage is reduced, better timing resolution is needed to produce artifact-free images. In particular, the present study indicates that a resolution of 600 ps or better was preferred for a ⅔ ring scanner (scanner ring diameter of 15-cm), while a timing resolution of 300 ps or better was preferred for the ½ ring scanner geometry, in order to achieve hot lesion CRC values similar to a full ring scanner. This suggests that there will eventually be a trade-off in the design of such PET scanners where the timing resolution will be determined by detector performance which, in turn, will define the minimum angular coverage needed in the scanner for artifact or distortion-free images without rotation.

In conclusion, it has been presently shown that TOF PET imaging can have an important application in the design of limited angle, application specific PET scanners. By producing distortion and artifact-free images one can avoid the need for detector rotation in order to achieve quantitative, tomographic images. This can have an impact in the design of not only dedicated scanners (e.g., breast, brain, prostate, or cardiac scanners), but also in-beam PET scanners for monitoring of dose delivery in proton and heavy-ion therapy machines.

REFERENCES

1. Alavi A, Kung J W, Zhuang H. Implications of PET based molecular imaging on the current and future practice of medicine. *Sem Nucl Med.* 56-69 2004; 34.
2. *Cancer Facts and Figures* 2007. Atlanta: American Cancer Society; 2007.
3. Palmedo H, Biersack H J, Lastoria S, et al. Scintimammography with technetium-99m methoxyisobutylisonitrile: results of a prospective European multicentre trial. *Eur J Nucl Med.* April 1998; 25(4):375-385.
4. Khalkhali I, Villanueva-Meyer J, Edell S L, et al. Diagnostic accuracy of Tc-99m-sestamibi breast imaging: Multi-center trial results. *J Nucl Med.* December 2000; 41(12): 1973-1979.
5. Avril N, Dose J, Janicke F, et al. Metabolic characterization of breast tumors with positron emission tomography using F-18 fluorodeoxyglucose. *J Clin Oncol.* June 1996; 14(6): 1848-1857.
6. Samson D J, Flamm C R, Pisano E D, Aronson N. Should FDG PET be used to decide whether a patient with an abnormal mammogram or breast finding at physical examination should undergo biopsy? *Acad Radiol.* July 2002; 9(7):773-783.
7. Kolb T M, Lichy J, Newhouse J H. Comparison of the performance of screening mammography, physical examination, and breast US and evaluation of factors that influence them: An analysis of 27,825 patient evaluations. *Radiol.* October 2002; 225(1):165-175.
8. Tarantola G, Zito F, Gerundini P. PET instrumentation and reconstruction algorithms in whole-body applications. *J Nucl Med.* May 2003; 44(5):756-769.
9. Humm J L, Rosenfeld A, Del Guerra A. From PET detectors to PET scanners. *Eur J Nucl Med.* November 2003; 30(11):1574-1597.
10. Avril N, Rose C A, Schelling M, et al. Breast imaging with positron emission tomography and fluorine-18 fluorodeoxyglucose: Use and limitations. *J Clin Oncol.* Oct. 15, 2000; 18(20):3495-3502.
11. Avril N, Bense S, Ziegler S I, et al. Breast imaging with fluorine-18-FDG PET: Quantitative image analysis. *J Nucl Med.* 1997; 38(8):1186-1191.
12. Hoffman E J, Huang S C, Phelps M E. Quantitation in Positron Emission Computed-Tomography 1. Effect of Object Size. *Journal of Computer Assisted Tomography.* 1979; 3(3):299-308.
13. Torizuka T, Zasadny K R, Recker B, Wahl R L. Untreated primary lung and breast cancers: Correlation between F-18 FDG kinetic rate constants and findings of in vitro studies. *Radiology.* June 1998; 207(3):767-774.
14. Quon A, Gambhir S S. FDG-PET and beyond: Molecular breast cancer imaging. *J Clin Oncol.* Mar. 10, 2005; 23(8): 1664-1673.
15. Yutani K, Shiba E, Kusuoka H, et al. Comparison of FDG-PET with MIBI-SPECT in the detection of breast cancer and axillary lymph node metastasis. *J Comput Assist Tomogr.* March-April 2000; 24(2):274-280.
16. Wahl R L. Current status of PET in breast cancer imaging, staging, and therapy. *Semin Roentg.* July 2001; 36(3):250-260.
17. Surti S, Karp J S, Freifelder R, Liu F. Optimizing the performance of a PET detector using discrete GSO crystals on a continuous lightguide. *IEEE Trans Nucl Sci.* 2000; 47:1030-1036.
18. Casey M E, Nutt R. A multicrystal two dimensional BGO detector system for positron emission tomography. *IEEE Trans Nucl Sci.* 1986; 33(1):460-463.
19. Wong W H, Uribe J, Hicks K, Zambelli M. A 2-Dimensional Detector Decoding Study on Bgo Arrays with Quadrant Sharing Photomultipliers. *IEEE Trans Nucl Sci.* August 1994; 41(4):1453-1457.
20. Surti S, Karp J S. Imaging characteristics of a 3-dimensional GSO whole-body PET camera. *Journal of Nuclear Medicine.* June 2004; 45(6):1040-1049.

21. Surti S, Karp J S, Perkins A E, Freifelder R, Muehllehner G. Design evaluation of A-PET: A high sensitivity animal PET camera. *IEEE Trans Nucl Sci*. October 2003; 50(5):1357-1363.

22. Surti S, Karp J S, Perkins A E, et al. Imaging performance of A-PET: A small animal PET camera. *IEEE Trans Med. Imag*. July 2005; 24(7):844-852.

23. Thompson C J, Murthy K, Weinberg I N, Mako F. Feasibility Study for Positron Emission Mammography. *Med. Phys*. April 1994; 21(4):529-538.

24. Thompson C J, Murthy K, Picard Y, Weinberg I N, Mako R. Positron Emission Mammography (PEM)—a Promising Technique for Detecting Breast-Cancer. *IEEE Trans Nucl Sci*. August 1995; 42(4):1012-1017.

25. Doshi N K, Shao Y P, Silverman R W, Cherry S R. Design and evaluation of an LSO PET detector for breast cancer imaging. *Med. Phys*. July 2000; 27(7):1535-1543.

26. Moses W W, Budinger T F, Huesman R H, Derenzo S E. PET camera designs for imaging breast cancer and axillary node involvement. *J Nucl Med*. 1995; 36:69P.

27. Weinberg I, Majewski S, Weisenberger A, et al. Preliminary results for positron emission mammography: Real-time functional breast imaging in a conventional mammography gantry. *Eur J Nucl Med*. July 1996; 23(7):804-806.

28. Raylman R R, Majewski S, Wojcik R, et al. The potential role of positron emission mammography for detection of breast cancer. A phantom study. *Med. Phys*. August 2000; 27(8):1943-1954.

29. Raylman R R, Majewski S, Weisenberger A G, et al. Positron emission mammography-guided breast biopsy. *J Nucl Med*. June 2001; 42(6):960-966.

30. Raylman R R, Majewski S, Weisenberger A, Popov V, Kross B, Wojcik R. Pixelated NaI(Tl) arrays for use in Positron Emission Mammography (PEM). *J Nucl Med*. May 2002; 43(5):11p-11p.

31. Raylman R R, Majewski S, Smith M F, et al. Comparison of scintillators for positron emission mammography (PEM) systems. *IEEE Trans Nucl Sci*. February 2003; 50(1):42-49.

32. Weinberg I, Beylin D, Yarnall S, et al. Applications of a PET device with 1.5 mm FWHM intrinsic spatial resolution to breast cancer imaging. Paper presented at: IEEE International Symposium on Biomedical Imaging: Macro to Nano, 2004, 2004; Arlington, Va.

33. Berg W A, Weinberg I N, Narayanan D, et al. High-Resolution Fluorodeoxyglucose Positron Emission Tomography with Compression ("Positron Emission Mammography") is Highly Accurate in Depicting Primary Breast Cancer. *The Breast Journal*. 2006; 12(4):309-323.

34. Levin C S, Foudray A M K, Habte F. Impact of high energy resolution detectors on the performance of a PET system dedicated to breast cancer imaging. *Physica Medica*. 2006; 21:28-34.

35. Yang Y F, Dokhale P A, Silverman R W, et al. Depth of interaction resolution measurements for a high resolution PET detector using position sensitive avalanche photo-diodes. *Phys Med Biol*. May 2006; 51(9):2131-2142.

36. Townsend D, Schorr B, Jeavons A. 3-Dimensional Image-Reconstruction for a Positron Camera with Limited Angular Acceptance. *IEEE Trans Nucl Sci*. 1980; 27(1):463-470.

37. MacDonald B, Perez-Mendez V, Tam K C. Contribution of time-of-flight information to limited angle positron tomography. *IEEE Trans Nucl Sci*. 1982; NS-29:516-519.

38. Muehllehner G, Buchin M P, Dudek J H. Performance Parameters of a Positron Imaging Camera. *IEEE Trans Nucl Sci*. 1976; 23(1):528-537.

39. Moses W W, Qi J. Fundamental limits of positron emission mammography. *Nucl Instrum Meth A*. January 2003; 497(1):82-89.

40. Freifelder R, Karp J S. Dedicated PET scanners for breast imaging. *Phys Med Biol*. December 1997; 42(12):2463-2480.

41. Freifelder R, Cardi C, Grigoras I, Saffer J R, Karp J S. First results of a dedicated breast PET imager (B-PET) using NaI(Tl) curve-plate detectors. Paper presented at: 2001 IEEE Nuclear Science Symposium and Medical Imaging Conference, 2001; San Diego, Calif.

42. Srinivas S M, Freifelder R, Saffer J R, et al. A Dedicated Breast Positron Emission Tomography (B-PET) Scanner: Characterization and Pilot Patient Study. Paper presented at: 2006 IEEE Nuclear Science Symposium and Medical Imaging Conference, 2006; San Diego, Calif.

43. Lamare F, Bowen S L, Visvikis D, et al. Design simulation of a rotating dual-headed PET/CT scanner for breast imaging. Paper presented at: IEEE Nuclear Science Symposium & Medical Imaging Conference, 2005; Puerto Rico, USA.

44. Conti M, Bendriem B, Casey M, et al. First experimental results of time-of-flight reconstruction on an LSO PET scanner. *Phys Med Biol*. Oct. 7, 2005; 50(19):4507-4526.

45. Karp J S, Kuhn A, Perkins A E, et al. Characterization of TOF PET scanner based on Lanthanum Bromide. Paper presented at: 2005 IEEE Nuclear Science Symposium and Medical Imaging Conference, 2005; San Juan, Puerto Rico.

46. Surti S, Kuhn A, Werner M E, Perkins A E, Kolthammer J, Karp J S. Performance of Philips Gemini TF PET/CT scanner with special consideration for its time-of-flight imaging capabilities. *J Nucl Med*. March 2007; 48(3):471-480.

47. Vandenberghe S, Daube-Witherspoon M E, Lewitt R M, Karp J S. Fast reconstruction of 3D time-of-flight PET data by axial rebinning and transverse mashing. *Phys Med. Biol*. March 2006; 51(6):1603-1621.

48. Vandenberghe S, Lemahieu I. System characteristics of simulated limited angle TOF PET. *Nucl Instr Meth (A)*. February 2007; 571(1-2):480-483.

49. Adam L E, Karp J S, Daube-Witherspoon M E, Smith R J. Performance of a whole-body PET scanner using curve-plate NaI(Tl) detectors. *J Nucl Med*. December 2001; 42(12):1821-1830.

50. Perkins A E, Muehllehner G, Surti S, Karp J S. Performance measurements of a pixelated NaI(Tl) PET scanner. *IEEE Trans Nucl Sci*. June 2003; 50(3):373-377.

51. Karp J S, Surti S, Daube-Witherspoon M E, et al. Performance of a brain PET camera based on anger-logic gadolinium oxyorthosilicate detectors. *J Nucl Med*. August 2003; 44(8):1340-1349.

52. Surti S, Karp J S. Imaging characteristics of a 3-dimensional GSO whole-body PET camera. *J Nucl Med*. June 2004; 45(6):1040-1049.

53. Karp J S, Muehllehner G. Performance of a Position-Sensitive Scintillation Detector. *Phys Med. Biol*. 1985; 30(7):643-655.

54. Mankoff D A, Muehllehner G, Karp J S. The High Count Rate Performance of a 2-Dimensionally Position-Sensitive Detector for Positron Emission Tomography. *Phys Med. Biol*. April 1989; 34(4):437-456.

55. Surti S, Karp J S. A count-rate model for PET scanners using pixelated Anger-logic detectors with different scintillators. *Phys Med. Biol*. 2005; 50:5697-5715.

56. Adam L E, Karp J S, Brix G. Investigation of scattered radiation in 3D whole-body positron emission tomography using Monte Carlo simulations. *Phys Med. Biol.* December 1999; 44(12):2879-2895.
57. Surti S, Karp J S, Muehllehner G. Image quality assessment of LaBr3-based whole-body 3D PET scanners: a Monte Carlo evaluation. *Phys Med Biol.* Oct. 7, 2004; 49(19):4593-4610.
58. Kuhn A, Surti S, Karp J S, et al. Design of a lanthanum bromide detector for time-of-flight PET. *IEEE Trans Nucl Sci.* October 2004; 51(5):2550-2557.
59. Surti S, Karp J S, Popescu L A, Daube-Witherspoon M E, Werner M. Investigation of time-of-flight benefit for fully 3-D PET. *IEEE Trans Med. Imag.* May 2006; 25(5):529-538.
60. Surti S, Kuhn A, Daube-Witherspoon M E, Werner M, Karp J S. Measurements for TOF image quality gain in 3D PET and its implications for clinical imaging. *J Nucl Med.* May 1, 2006 2006; 47.
61. Surti S, Karp J S, Muehllehner G. Evaluation of pixelated NaI(Tl) detectors for PET. *IEEE Trans Nucl Sci.* February 2003; 50(1):24-31.
62. Kuhn A, Surti S, Shah K S, Karp J S. Investigation of LaBr3 Detector Timing Resolution. Paper presented at: 2005 IEEE Nuclear Science Symposium and Medical Imaging Conference, 2005; San Juan, Puerto Rico.
63. Kyba C C M, Wiener R I, Newcomer F M, Van Berg R, Dressnandt N, Karp J S. Timing measurements from TOF-PET scanner using local PMT triggering. Paper presented at: 2007 IEEE Nuclear Science Symposium and Medical Imaging Conference, 2007; Honololu, Hi.
64. Wong W H, Uribe, J., Hicks, K., Hu, G. An analog decoding BGO block detector using circular photomultipliers. *IEEE Trans Nucl Sci.* 1995; 42:1095-1101.
65. *NEMA Standards Publication NU 2-2001, Performance Measurements of Positron Emission Tomographs.* Washington, D.C.: National Electrical Manufacturers Association; 2001.
66. Moses W W, Derenzo S E. Prospects for time-of-flight PET using LSO scintillator. *IEEE Trans Nucl Sci.* June 1999; 46(3):474-478.
67. Chen C, Jones M, Kononenko W, et al. Front-end electronics for the CDF-II time-of-flight system. *IEEE Trans Nucl Sci.* 2003; 50(6):2486-2490.
68. Wong W H, Mullani N A, Wardworth G, Hartz R K, Bristow D. Characteristics of Small Barium Fluoride (BaF2) Scintillator for High Intrinsic Resolution Time-of-Flight Positron Emission Tomography. *IEEE Trans Nucl Sci.* 1984; 31(1):381-386.
69. Moriya T, Omura T, Watanabe M, Yamashita T. Development of a position-sensitive detector for TOF-PET. Paper presented at: 2007 IEEE Nuclear Science Symposium and Medical Imaging Conference, 2007; Honolulu, Hi.
70. Yoshizawa Y. Recent progress in PMTs. Paper presented at: LIGHT07 Workshop, 2007; Tegernsee, Germany.
71. Budinger T F. Time-of-Flight Positron Emission Tomography—Status Relative to Conventional PET. *J Nucl Med.* 1983; 24(1):73-76.
72. Barrett H H, Yao J, Rolland J P, Myers K J. Model observers for assessment of image quality. *Proc Natl Acad Sci.* 1993; 90:9758-9765.
73. Eckstein M P, Abbey C K, Bochud F O. A practical guide to model observers for visual detection in synthetic and natural noisy image. In: Beutel J, Kundel H K, Metter R L V, eds. *Handbook of Medical Imaging: Vol.* 1, *Physics and Psychophysics.* Vol 1. Bellingham, Wash.: SPIE Press; 2000:593-628.
74. Abbey C K, Bochud F O. Modeling visual detection tasks in correlated image noise with linear model observers. In: Beutel J, Kundel H K, Metter R L V, eds. *Handbook of Medical Imaging: Vol.* 1, *Physics and Psychophysics.* Vol 1. Bellingham, Wash.: SPIE Press; 2000:629-654.
75. Myers K J, Rolland J P, Barrett H H, Wagner R F. Aperture optimization for emission imaging: Effects of spatially varying background. *J Opt Soc Am A.* 1990; 7:1279-1293.
76. Burgess A E, Li X, Abbey C K. Visual signal detectability with two noise components: Anomalous masking effects. *J Opt Soc Am A.* 1997; 14:2420-2442.
77. Tapiovaara M J, Wagner R F. SNR and noise measurements for medical imaging: I. A practical approach based on statistical decision theory. *Phys Med. Biol.* 1993; 38:71-92.
78. Hanson K M. Detectability in computed tomographic image. *Med. Phys.* 1980; 6:441-451.
79. Wagner R F, K. E. W. An assortment of image quality indices for radiographic film-screen combinations—Can they be resolved? *SPIE Proceedings.* 1972; 35:83-94.
80. Ishida M, Doi K, Loo L, Metz C E. Digital image processing: Effect on detectability of simulated low-contrast radiographic patterns. *Radiol.* 1984; 150:569-575.
81. Myers M J. *Visual perception in correlated noise* [PhD thesis]. Tucson, Ariz., University of Arizona; 1985.
82. Wollenweber S D, Tsui B M W, Lalush D S, Frey E C, LaCroix K J, Gullberg G T. Comparison of Hotelling observer models and human observers in defect detection from myocardial SPECT imaging. *IEEE Trans Nucl Sci.* 1999; 46:2098-2108.
83. Gifford H C, King M A, De Vries D J, Soares E J. Channelized Hotelling and human observer correlation for lesion detection in hepatic SPECT imaging. *J Nucl Med.* 2000; 41:514-521.
84. Myers K J, Barrett H H. Addition of a channel mechanism to the ideal-observer model. *J Opt Soc Am A.* 1987; 4:2447-2457.
85. Barrett H H, Abbey C K, Gallas B. Stabilized estimates of Hotelling-observer detection performance in patient-structured noise. *SPIE Proceedings.* 1998; 3340:27-43.
86. Gifford H C, Wells R G, King M A. A comparison of human observer LROC and numerical observer ROC for tumor detection in SPECT images. *IEEE Trans Nucl Sci.* 1999; 46:1032-1037.
87. Gifford H C, Farncombe T H, King M A. Ga-67 tumor detection using penalized-EM with nonanatomical regularizers. Paper presented at: Conference Record of 2002 Nuclear Science Symposium and Medical Imaging Conference, 2002.
88. Gifford H C, King M A, Pretorius P H, Wells R G. A comparison of human and model observers in multislice LROC studies. *IEEE Trans Med. Imag.* 2005; 24:160-169.
89. Barrett H H, Myers K J. *Foundations of Image Science.* Hoboken, N.J.: John Wiley & Sons; 2004.
90. Abbey C K, Barrett H H. Human- and model-observer performance in ramp-spectrum noise: Effects of regularization and object variability. *J Opt Soc Am A.* 2001; 18:473-488.
91. Matej S, Lewitt R M. Direct Fourier reconstruction with Fourier reprojection for fully 3-D PET. *IEEE Trans Nucl Sci.* 2001; 48:1378-1385.
92. Werner M E, Surti S, Karp J S. Implementation and Evaluation of a 3D PET Single Scatter Simulation with TOF Modeling. Paper presented at: 2006 IEEE Nuclear Science Symposium and Medical Imaging Conference, 2006; San Diego, Calif.

93. Popescu L M. Iterative image reconstruction using geometrically ordered subsets with list-mode data. Paper presented at: 2004 IEEE Nuclear Science Symposium and Medical Imaging Conference, 2004; Rome, Italy.
94. Matej S, Lewitt R M. Efficient 3D grids for image-reconstruction using spherically-symmetrical volume elements. *IEEE Trans Nucl Sci*. 1995; 42(4):1361-1370.
95. Tai Y C, Chatziioannou A F, Yang Y F, et al. MicroPET II: design, development and initial performance of an improved microPET scanner for small-animal imaging. *Phys Med. Biol*. Jun. 7, 2003; 48(11):1519-1537.

What is claimed:

1. A time-of-flight positron emission tomography device comprising:
a detector array having more than two detector segments configured to accommodate a body part and to acquire tracer emission signals from a target within an imaging situs with a timing resolution of less than about 600 ps and without rotation of said detector array, wherein said segments are asymmetrically distributed about a space defining a ring around the imaging situs; and
a processor that receives said acquired signals from said detector array and converts said signals into a three dimensional, tomographic image reconstruction of said target.

2. The device according to claim 1 wherein said timing resolution is about 300 ps to about 600 ps.

3. The device according to claim 2 wherein said detector array occupies about 50% of a space defining a ring around said imaging situs.

4. The device according to claim 2 wherein said detector array occupies about ⅔ of a space defining a ring around said imaging situs.

5. The device according to claim 1 wherein said timing resolution is less than about 300 ps.

6. The device according to claim 5 wherein said detector array occupies less than 50% of a space defining a ring around said imaging situs.

7. The device according to claim 1 comprising four detector segments.

8. The device according to claim 1 wherein said ring is circular, elliptical, irregular, or a regular polygon with four equal sides.

9. The device according to claim 1 wherein the maximum distance between said detector segments is no more than about 40 cm during the operation of said device.

10. The device according to claim 1 wherein said detector array comprises curvilinear detector segments.

11. The device according to claim 1 wherein said detector array comprises rectilinear detector segments.

12. The device according to claim 1 wherein said detector array is configured to accommodate a breast.

13. The device according to claim 1 wherein said detector array is configured for cardiac imaging.

14. The device according to claim 1 wherein said detector array is configured for brain imaging.

15. The device according to claim 1 wherein said detector array is configured for prostate imaging.

16. The device according to claim 1 wherein said detector array is configured such that said detector segments are movable relative to one another.

17. The device according to claim 1 wherein said detector array comprises scintillator crystals of lutetium oxyorthosilicate, lutetium yttrium oxyorthosilicate, or lanthanum bromide.

18. The device according to claim 17 wherein each of said crystals have a length of about 10 to about 30 mm.

19. The device according to claim 18 wherein each of said crystals have an individual size of 4×6×20 mm³.

20. The device according to claim 18 wherein each of said crystals have an individual size of 2×2×10 mm³.

21. The device according to claim 17 wherein each of said crystals have a polished surface finish.

22. The device according to claim 1 wherein each of said detector segments are coupled to a photodetector array.

23. The device according to claim 22 wherein each of said detector segments are coupled to a photodetector array via a continuous lightguide.

24. The device according to claim 23 wherein said photodetector array comprises a plurality of single-channel photomultiplier tubes.

25. The device according to claim 23 wherein said photodetector array comprises a plurality of multi-anode photomultiplier tubes.

26. The device according to claim 23 wherein said photodetector array comprises a plurality of position-sensitive photomultiplier tubes.

27. The device according to claim 23 wherein said photodetector array comprises a plurality of silicon photomultiplier tubes.

28. The device according to claim 1 further comprising a mammography unit, an optical imaging array, or both.

29. A time-of-flight positron emission tomography device comprising:
a detector array comprising two detector segments configured to accommodate a body part and to acquire tracer emission signals from a target within an imaging situs with a timing resolution of less than about 600 ps and without rotation of said detector array, wherein the maximum distance between said segments is no more than about 40 cm during the operation of said device; and
a processor that receives said acquired signals from said detector array and converts said signals into a three dimensional, tomographic image reconstruction of said target.

30. The device according to claim 29 wherein said timing resolution is about 300 ps to about 600 ps.

31. The device according to claim 29 wherein said timing resolution is less than about 300 ps.

32. The device according to claim 31 wherein said detector array occupies less than 50% of a space defining a ring around said imaging situs.

33. The device according to claim 29 wherein said detector array comprises separate detector segments that are symmetrically distributed about a space defining a ring around said imaging situs.

34. The device according to claim 33 wherein said ring is circular, elliptical, irregular, or a regular polygon with four equal sides.

35. The device according to claim 29 wherein said detector array comprises separate detector segments that are asymmetrically distributed about a space defining a ring around said imaging situs.

36. The device according to claim 35 wherein said ring is circular, elliptical, or irregular.

37. The device according to claim 29 wherein said detector array comprises curvilinear detector segments.

38. The device according to claim 29 wherein said detector array comprises rectilinear detector segments.

39. The device according to claim 29 wherein said detector array is configured to accommodate a breast, for cardiac imaging, for brain imaging, or for prostate imaging.

40. The device according to claim 29 wherein said detector array comprises scintillator crystals of lutetium oxyorthosilicate, lutetium yttrium oxyorthosilicate, or lanthanum bromide.

41. The device according to claim 40 wherein each of said crystals have a length of about 10 to about 30 mm.

42. The device according to claim 41 wherein each of said crystals have an individual size of 4×6×20 mm$^3$.

43. The device according to claim 41 wherein each of said crystals have an individual size of 2×2×10 mm$^3$.

44. The device according to claim 29 wherein each of said detector segments are coupled to a photodetector array.

45. A time-of-flight positron emission tomography device comprising:
   a detector array having at least two detector segments configured to accommodate a body part and to acquire tracer emission signals from a target within an imaging situs with a timing resolution of less than about 600 ps and without rotation of said detector array,
   wherein said detector array comprises scintillator crystals of lutetium oxyorthosilicate, lutetium yttrium oxyorthosilicate, or lanthanum bromide having a length of about 10 to about 30 mm and an individual size of 4×6×20 mm$^3$; and
   a processor that receives said acquired signals from said detector array and converts said signals into a three dimensional, tomographic image reconstruction of said target.

46. The device according to claim 45 wherein said timing resolution is about 300 ps to about 600 ps.

47. The device according to claim 45 wherein said timing resolution is less than about 300 ps.

48. The device according to claim 47 wherein said detector array occupies less than 50% of a space defining a ring around said imaging situs.

49. The device according to claim 45 wherein said detector array comprises separate detector segments that are symmetrically distributed about a space defining a ring around said imaging situs.

50. The device according to claim 49 wherein said ring is circular, elliptical, irregular, or a regular polygon with four equal sides.

51. The device according to claim 46 wherein said detector array comprises separate detector segments that are asymmetrically distributed about a space defining a ring around said imaging situs.

52. The device according to claim 51 wherein said ring is circular, elliptical, or irregular.

53. The device according to claim 45 wherein said detector array comprises curvilinear detector segments.

54. The device according to claim 45 wherein said detector array comprises rectilinear detector segments.

55. The device according to claim 45 wherein said detector array is configured to accommodate a breast, for cardiac imaging, for brain imaging, or for prostate imaging.

56. The device according to claim 45 wherein each of said crystals have an individual size of 2×2×10 mm$^3$.

57. The device according to claim 45 wherein each of said detector segments are coupled to a photodetector array.

* * * * *